United States Patent
Kang et al.

(10) Patent No.: US 7,763,648 B2
(45) Date of Patent: Jul. 27, 2010

(54) OXA-STEROIDS DERIVATIVES AS SELECTIVE PROGESTERONE RECEPTOR MODULATORS

(75) Inventors: Fu-An Kang, Exton, PA (US);
Nareshkumar F. Jain, Exton, PA (US);
Zhihua Sui, Exton, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 693 days.

(21) Appl. No.: 11/675,741

(22) Filed: Feb. 16, 2007

(65) Prior Publication Data

US 2007/0197635 A1 Aug. 23, 2007

Related U.S. Application Data

(60) Provisional application No. 60/775,042, filed on Feb. 17, 2006.

(51) Int. Cl.
*A61K 31/35* (2006.01)
*C07D 311/94* (2006.01)

(52) U.S. Cl. ...................... 514/453; 549/383

(58) Field of Classification Search ................ 549/383; 514/453

See application file for complete search history.

(56) References Cited

U.S. PATENT DOCUMENTS 3,962,275 A    6/1976  Guthrie et al.

FOREIGN PATENT DOCUMENTS

EP    0057115    8/1982

OTHER PUBLICATIONS

Bucourt, R. et al.: "Heterocyclic 19-Norsteroids.I. Total Synthesis of 3-oxo-7-oxa-19-norsteroids". Bulletin De La Societe Chimique De France, (3-4, pt. 2), 896-900, XP002451831, (1975).
Cook, C.E. et al.: "Reversal of Activity Profile in Analogs of the Antiprogestin RU 486: Effect of a 16α-Substituent on Progestational (Agonist) Activity"; Life Sciences (1993) 52: 155-162.
Kang, et al.: "Synthesis and Identification of Novel Oxa-Steroids as Progesterone Receptor Antagonists". Bioorganic & Medicinal Chemistry Letters, Oxford, GB, vol. 17, No. 4, Feb. 1, 2007, XP005868807.
Kang, et al.: "Parallel Synthesis and SAR Study of Novel-Oxa-Steroids as Potent and Selective Progesterone Receptor Antagonists". Bioorganic & Medicinal Chemistry Letters, Oxford, GB, vol. 17, No. 9, Apr. 3, 2007, XP022015338.
Wagner, B.L. et al.: "16α-substituted analogs of the antiprogestin RU486 induce a unique conformation in the human progesterone receptor resulting in mixed agonist activity"; Proc. Natl. Acad Sci. USA, (1996) 93: 8739-8744.

*Primary Examiner*—Janet L. Andres
*Assistant Examiner*—Raymond Covington
(74) *Attorney, Agent, or Firm*—Yuriy P. Stercho

(57) ABSTRACT

The present invention is directed to 7 oxa-estra-4,9-diene-3,17-dione derivatives, pharmaceutical compositions containing them and their use in the treatment of disorders and conditions modulated by at least one progesterone or glucocorticoid receptor.

13 Claims, No Drawings

OXA-STEROIDS DERIVATIVES AS SELECTIVE PROGESTERONE RECEPTOR MODULATORS

CROSS REFERENCE TO RELATED APPLICATIONS

This application claims the benefit of U.S. Provisional Application 60/775,042, filed on Feb. 17, 2006, which is incorporated by reference herein in its entirety.

FIELD OF THE INVENTION

The present invention is directed to novel 7-oxa-estra-4,9-diene-3,17-dione derivatives, pharmaceutical compositions containing them and their use in the treatment of disorders and conditions modulated by at least one progesterone or glucorticoid receptor. More particularly, the compounds of the present invention are useful in the treatment of disorders including, but not limited to, secondary amenorrhea; dysfunctional bleeding; uterine leiomyomata; endometriosis; polycystic ovary syndrome; carcinomas and adenocarcinomas of the endometrium, ovary, breast, colon and/or prostate, Type II diabetes mellitus, impaired oral glucose tolerance, elevated blood glucose levels and Syndrome X. The compounds of the present invention are further useful as contraceptives and for the minimization of side effects of cyclic menstrual bleeding (e.g. for the treatment of premenstrual syndrome) and for contraception.

BACKGROUND OF THE INVENTION

Intracellular receptors are a class of structurally related proteins involved in the regulation of gene proteins. Steroid receptors are a subset of these receptors, including the progesterone receptors (PR), androgen receptors (AR), estrogen receptors (ER), glucocorticoid receptors (GR) and mineralocorticoid receptors (MR). Regulation of a gene by such factors requires the intracellular receptor and corresponding ligands, which has the ability to selectively bind to the receptor in a way that affects gene transcription.

Progesterone receptor modulators (progestagens) are known to play an important role in mammalian development and homeostasis. Progesterone is known to be required for mammary gland development, ovulation and the maintenance of pregnancy. Currently, steroidal progestin agonists and antagonists are clinically approved for contraception, hormone replacement therapy (HRT) and therapeutic abortion. Moreover, there is good preclinical and clinical evidence for the value of progestin antagonists in treating endometriosis, uterine leiomyomata (fibroids), dysfunctional uterine bleeding and breast cancer.

The current steroidal progestagens have been proven to be quite safe and are well tolerated. Sometimes, however, side effects (e.g. breast tenderness, headaches, depression and weight gain) have been reported that are attributed to these steroidal progestagens, either alone or in combination with estrogenic compounds.

Steroidal ligands for one receptor often show cross-reactivity with other steroidal receptors. As an example, many progestagens also bind to glucocorticoid receptor. Non-steroidal progestagens have no molecular similarity with steroids and therefore one might also expect differences in physicochemical properties, pharmacokinetic (PK) parameters, tissue distribution (e.g. CNS versus peripheral) and, more importantly, non-steroidal progestagens may show no/less cross-reactivity to other steroid receptors. Therefore, non-steroidal progestagens will likely emerge as major players in reproductive pharmacology in the foreseeable future.

It was known that progesterone receptor existed as two isoforms, full-length progesterone receptor isoform (PR-B) and its shorter counterpart (PR-A). Recently, extensive studies have been implemented on the progesterone receptor knockout mouse (PRKO, lacking both the A- and B-forms of the receptors), the mouse knockoutting specifically for the PR-A isoform (PRAKO) and the PR-β isoform (PRBKO). Different phenotypes were discovered for PRKO, PRAKO and PRBKO in physiology studies in terms of fertility, ovulation uterine receptivity, uterine proliferation, proliferation of mammary gland, sexual receptivity in female mice, sexual activity in male mice and infanticide tendencies in male mice. These findings provided insights for synthetic chemists to construct not only selective progesterone receptor modulator (SPRM), but also PR-A or PR-B selective progesterone receptor modulator.

Progesterone plays a major role in reproductive health and functioning. Its effects on, for example, the uterus, breast, cervix and hypothalamic-pituitary unit are well established. The actions of progesterone as well as progesterone antagonists are mediated by the progesterone receptor (PR). In the target cell, progesterone produces a dramatic change in confirmation of the PR that is associated with transforming the PR from a non-DNA binding form to one that will bind to DNA. This transformation is accompanied by a loss of associated heat shock proteins and dimerization. The activated PR dimmer then binds to specific DNA sequences within the promotor region of progesterone responsive genes. The agonist-bound PR is believed to activate transcription by associating with coactivators, which act as bridging factors between the receptor and the general transcription machinery. This is followed by increases in the rate of transcription producing agonist effects at the cellular and tissue levels. These progesterone receptor ligands exhibit a spectrum of activity ranging from pure antagonists to mixed agonists/antagonists.

In 1982, the discovery of compounds that bind to the progesterone receptor, antagonize the effects of progesterone receptor and antagonize the effects of progesterone was announced. Although compounds such as estrogens and certain enzyme inhibitors can prevent the physiological effects of endogenous progesterone, the term "antiprogestin" is confined to those compounds that bind to the progestin receptor. A report from the Institute of Medicine (Donaldson, Molly S.; Dorflinger, L.; Brown, Sarah S.; Benet, Leslie Z., Editors, *Clinical Applications of Mifepristone (RU 486) and Other antiprogestins*, Committee on antiprogestins: Assessing the science, Institute of medicine, National Academy Press, 1993) summarized a number of medical conditions related to the effect of antiprogestins. In view of the pivotal role that progesterone plays in reproduction, it is not surprising that antiprogestins could play a part in fertility control, including contraception, menses induction and medical termination of pregnancy, but there are many other potential uses that have been supported by small clinical or preclinical studies, such as labor and delivery; treatment of uterine leiomyomas (fibroids), treatment of endometriosis; HRT; breast cancers; male contraception, etc.

The effects and uses of progesterone agonists have been well established. In addition, it has been recently shown that certain compounds structurally related to the known antiprogestins have agonist activity in certain biological systems (e.g., the classical progestin effects I the estrogen-primed immature rabbit uterus; cf. C. E. Cook et al., Life Sciences, 52, 155-162 (1993)). Such compounds are partial agonists in human cell-derived receptor systems, where they bind to a site distinct from both the progestin and antiprogestin sites (Wagner et al., Proc. Natl. Acad. Sci., 93, 8739-8744 (1996)). Thus the general class of antiprogestins can have subclasses, which may vary in their clinical profiles.

Compounds which mimic some of the effects of progesterone (agonists), antagonize these effects (antagonists, antiprogestins) or exhibit mixed effects (partial agonists or mixed agonist/antagonist), known as progesterone receptor modulators (PRMs) can be useful in treating a variety of disease states and conditions. PR agonists have been used in female contraceptives and in postmenopausal hormone therapy. Recent studies in women and non-human primates show that PR antagonists may also have potential as contraceptive agents and for the treatment of various gynecological and obstetric diseases, including fibroids, endometriosis and, possibly, hormone-dependent cancers. Clinically available PR agonists and antagonists are steroidal compounds and often cause various side effects due to their functional interaction with other steroid receptors. Recently, numerous receptor-selective non-steroidal PR agonists and antagonists have emerged. Non-steroidal PR antagonists, being structurally distinct from the steroid class, may have greater potential for selectivity against other steroid receptors.

SUMMARY OF THE INVENTION

The present invention is directed to compounds of formula (I)

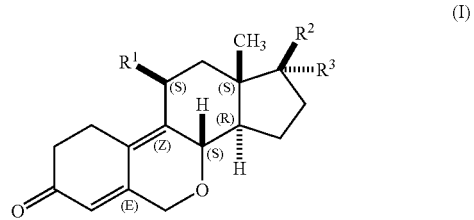

wherein $R^1$ is selected from the group consisting of $C_{1-6}$alkyl, $C_{2-4}$alkenyl, $C_{2-4}$alkynyl, aryl, heteroaryl, aralkyl and $C_{1-4}$alkyl-heteroaryl; wherein the aryl or heteroaryl, whether alone or as part of a substituent group is optionally substituted with one or more substituents independently selected from hydroxy, carboxy, halogen, $C_{1-4}$alkyl, halogenated $C_{1-4}$alkyl, $C_{1-4}$alkoxy, halogenated $C_{1-4}$alkoxy, cyano, nitro, amino, $(C_{1-4}$alkylamino) and di($C_{1-4}$alkyl)amino;

$R^2$ is selected from the group consisting of $OR^A$, $NR^AR^B$, $SR^A$ and $-SO_2-R^A$; wherein $R^A$ and $R^B$ are each independently selected from the group consisting of hydrogen and $C_{1-4}$alkyl;

$R^3$ is selected from the group consisting of $C_{1-6}$alkyl, $C_{2-4}$alkenyl, $C_{2-4}$alkynyl, aryl, heteroaryl and $-CC-R^4$;

$R^4$ is selected from the group consisting of $C_{1-6}$alkyl, $C_{1-4}$alkyl-OH, $C_{1-4}$alkyl-$NR^CR^D$, halogenated $C_{1-4}$alkyl, $C_{1-4}$alkyl-O—$C_{1-4}$alkyl, $C_{3-8}$cycloalkyl, aryl and heteroaryl; wherein the aryl or heteroaryl is optionally substituted with one or more substituents independently selected from hydroxy, carboxy, halogen, $C_{1-4}$alkyl, halogenated $C_{1-4}$alkyl, $C_{1-4}$alkoxy, halogenated $C_{1-4}$alkoxy, cyano, nitro, amino, $(C_{1-4}$alkylamino) and di($C_{1-4}$alkyl)amino; and wherein $R^C$ and $R^D$ are each independently selected from the group consisting of hydrogen and $C_{1-4}$alkyl;

and pharmaceutically acceptable salts esters and pro-drugs thereof.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by at least one progesterone receptor comprising administering to a subject in need thereof a therapeutically effective amount of any of the compounds or pharmaceutical compositions described above.

In another embodiment, the compounds of the present invention are useful for the treatment of disorders mediated by at least one glucocorticoid receptor comprising administering to a subject in need thereof a therapeutically effective amount of any of the compounds or pharmaceutical compositions described above.

In another embodiment, the compounds of the present invention are useful for the treatment of a disorder selected from the group consisting of secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding or for contraception; comprising administering to a subject in need thereof a therapeutically effective amount of any of the compounds or pharmaceutical compositions described above.

In another embodiment, the compounds of the present invention are useful for the treatment of a disorder selected from the group consisting of Type II diabetes mellitus, impaired oral glucose tolerance, elevated blood glucose levels and Syndrome X; comprising administering to a subject in need thereof a therapeutically effective amount of any of the compounds or pharmaceutical compositions described above.

Another example of the invention is the use of any of the compounds described herein in the preparation of a medicament for treating of a progesterone or glucocorticoid receptor mediated disorder, (treating a disorder selected from (a) secondary amenorrhea; (b) dysfunctional bleeding; (c) uterine leiomyomata; (d) endometriosis; (e) polycystic ovary syndrome; (f) carcinoma of the endometrium, (g) carcinoma of the ovary, (h) carcinoma of the breast, (i) carcinoma of the colon, (j) carcinoma of the prostate, (k) adenocarcinomas of the ovary, (l) adenocarcinomas of the breast, (m) adenocarcinomas of the colon, (n) adenocarcinomas of the prostate, (o) side effects of cyclic menstrual bleeding, (p) Type II diabetes mellitus, (q) impaired oral glucose tolerance, (r) elevated blood glucose levels, (s) Syndrome X or (t) for contraception, in a subject in need thereof) in a subject in need thereof.

DETAILED DESCRIPTION OF THE INVENTION

The present invention is directed to compounds of formula (I)

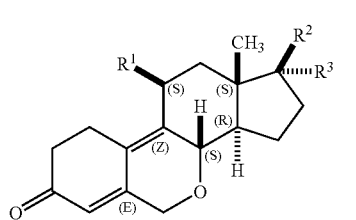

wherein R¹, R² and R³ are as herein defined. The compounds of formula (I) of the present invention are useful as progesterone receptor modulators and/or glucocorticoid receptor modulators, useful in the treatment of disorders including, but not limited to, secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding, Type II diabetes mellitus, impaired oral glucose tolerance, elevated blood glucose levels and Syndrome X or for contraception.

In an embodiment of the present invention, $R^1$ is selected from the group consisting of $C_{1-6}$alkyl, $C_{2-4}$alkenyl, $C_{2-4}$alkynyl, aryl and heteroaryl; wherein the aryl is optionally substituted with one or more substituents independently selected from halogen, $C_{1-4}$alkyl, fluorinated $C_{1-4}$alkyl, $C_{1-4}$alkoxy, fluorinated $C_{1-4}$alkoxy, cyano, nitro, amino, $(C_{1-4}$alkylamino) and di$(C_{1-4}$alkyl)amino.

In another embodiment of the present invention, $R^1$ is selected from the group consisting of $C_{1-4}$alkyl, $C_{2-4}$alkenyl, phenyl and 5- to 6-membered heteroaryl; wherein the phenyl is optionally substituted with a substituent selected from the group consisting of $C_{1-4}$alkyl, $C_{1-3}$alkoxy, nitro, amino, $(C_{1-4}$alkylamino) and di$(C_{1-4}$alkyl)amino. In another embodiment of the present invention, $R^1$ is selected from the group consisting of phenyl and 5- to 6-membered heteroaryl; wherein the phenyl is optionally substituted with a substituent selected from the group consisting of $C_{1-3}$alkoxy, amino, $(C_{1-4}$alkylamino) and di$(C_{1-4}$alkyl)amino.

In another embodiment of the present invention, $R^1$ is selected from the group consisting of isopropyl, isopropenyl, phenyl, 4-dimethylamino-phenyl, 4-methoxy-phenyl, 4-nitrophenyl, 4-isopropyl-phenyl and 2-thienyl. In another embodiment of the present invention, $R^1$ is selected from the group consisting of 4-dimethylamino-phenyl and 4-methoxy-phenyl.

In another embodiment of the present invention, $R^1$ is 4-dimethylamino-phenyl.

In an embodiment of the present invention, $R^2$ is selected from the group consisting of $OR^A$, $SR^A$ and $—SO_2—R^A$; wherein $R^A$ is selected from the group consisting of hydrogen and $C_{1-4}$alkyl. In another embodiment of the present invention, $R^2$ is $NR^AR^B$; wherein $R^A$ and $R^B$ are each independently selected from the group consisting of hydrogen and $C_{1-4}$alkyl. In another embodiment of the present invention, $R^2$ is selected from the group consisting of $SR^A$ and $SO_2R^A$.

In another embodiment of the present invention, $R^2$ is —OH. In yet another embodiment of the present invention, $R^2$ is (S)—OH.

In an embodiment of the present invention, $R^3$ is selected from the group consisting of $C_{1-6}$alkyl, $C_{2-4}$alkenyl, $C_{2-4}$alkynyl, phenyl, 5- to 6-membered heteroaryl and —CC—$R^4$.

In another embodiment of the present invention, $R^3$ is selected from the group consisting of $C_{1-4}$alkyl, $C_{2-4}$alkenyl, $C_{2-4}$alkynyl, phenyl and —CC—$R^4$. In another embodiment of the present invention, $R^3$ is selected from the group consisting of $C_{1-4}$alkyl, $C_{2-4}$alkenyl, $C_{2-4}$alkynyl and —CC—$R^4$.

In another embodiment of the present invention, $R^3$ is selected from the group consisting of —CH(CH₃)₂, —CH₂—CH₂—CH₃, —CH₂=CH₂, —CH₂—CH₂=CH₂, —C(CH₃)=CH₂, —CCH, —CC—CH₃, phenyl and —CC—$R^4$. In another embodiment of the present invention, $R^3$ is selected from the group consisting of —CH₂—CH₂—CH₃, —CH₂=CH₂, —CH₂—CH₂=CH₂, —CCH, —CC—CH₃ and —CC—$R^4$.

In another embodiment of the present invention, $R^3$ is —CC—$R^4$.

In an embodiment of the present invention, $R^4$ is selected from the group consisting of $C_{1-6}$alkyl, $C_{1-4}$alkyl-OH, $C_{1-4}$alkyl-NR$^C$R$^D$, fluorinated $C_{1-4}$alkyl, $C_{1-4}$alkyl-O—$C_{1-4}$alkyl, $C_{3-8}$cycloalkyl, aryl and heteroaryl; wherein the aryl is optionally substituted with one to three substituents independently selected from halogen, $C_{1-4}$alkyl, fluorinated $C_{1-4}$alkyl, $C_{1-4}$alkoxy, fluorinated $C_{1-4}$alkoxy, cyano, nitro, amino, $(C_{1-4}$alkylamino) and di$(C_{1-4}$alkyl)amino; and wherein R$^C$ and R$^D$ are each independently selected from the group consisting of hydrogen and $C_{1-4}$alkyl.

In another embodiment of the present invention, $R^4$ is selected from the group consisting of $C_{1-4}$alkyl, —$C_{1-4}$alkyl-OH, fluorinated $C_{1-3}$alkyl, —$C_{1-3}$alkyl-O—$C_{1-3}$alkyl, —$C_{1-4}$alkyl-NR$^C$R$^D$, $C_{3-8}$cycloalkyl, phenyl and 5- to 6-membered heteroaryl; wherein the phenyl is optionally substituted with one to two substituents independently selected from the group consisting of halogen, $C_{1-4}$alkyl, $C_{1-2}$alkyl, fluorinated $C_{1-2}$alkyl and cyano; and wherein R$^C$ and R$^D$ are each independently selected from hydrogen or $C_{1-2}$alkyl.

In another embodiment of the present invention, $R^4$ is selected from the group consisting of t-butyl, —C(CH₃)₂—OH, trifluoromethyl, methoxy-methyl-, dimethylamino-methyl-, cyclopropyl, phenyl, 2-methylphenyl, 3-methylphenyl, 4-methylphenyl, 4-t-butylphenyl, 4-methoxyphenyl, 2-trifluoromethylphenyl, 3-trifluoromethylphenyl, 4-trifluoromethylphenyl, 2-fluorophenyl, 3-fluorophenyl, 4-fluorophenyl, 3,5-difluorophenyl, 2-chlorophenyl, 3-chlorophenyl, 4-chlorophenyl, 2-bromophenyl, 4-bromophenyl, 4-cyanophenyl, 2-pyridyl, 3-pyridyl, 4-pyridyl and 3-thienyl.

In another embodiment of the present invention, $R^4$ is selected from the group consisting of phenyl, 3-methylphenyl, 4-methylphenyl, 4-methoxyphenyl, 2-fluorophenyl, 3-fluorophenyl, 4-fluorophenyl, 3,5-fuorophenyl, 2-chlorophenyl, 4-chlorophenyl, 4-bromophenyl, 2-trifluoromethylphenyl, 3-trifluoromethylphenyl, 4-trifluoromethylphenyl, 4-cyanophenyl and 3-thineyl.

In another embodiment of the present invention, $R^4$ is selected from the group consisting of trifluoromethyl, cyclopropyl, 3-methylphenyl, 4-methylphenyl, 3-fluorophenyl, 4-fluorophenyl, 3,5-difluorophenyl, 3-chlorophenyl, 4-chlorophenyl, 4-bromophenyl, 2-trifluoromethylphenyl, 3-trifluoromethylphenyl, 4-cyanophenyl and 3-thienyl.

In another embodiment of the present invention is any single compound or subset of compounds selected from the representative compounds listed in Tables 1 below.

Additional embodiments of the present invention, include those wherein the substituents selected for one or more of the variables defined herein (i.e. $R^1$, $R^2$ and $R^3$) are independently selected to be any individual substituent or any subset of substituents selected from the complete list as defined herein.

Representative compounds of the present invention are as listed in Table 1.

TABLE 1

Representative Compounds of Formula (I)

| ID No. | $R^3$ | Measured MW |
|---|---|---|
| 1 | methyl | 431.6 |
| 2 | cyclopropyl | 457.6 |
| 3 | phenyl | 493.7 |
| 4 | H | 417.6 |
| 5 | t-butyl | 473.7 |
| 6 | —C(CH$_3$)$_2$—OH | 475.6 |
| 7 | 4-methylphenyl | 507.7 |
| 8 | 4-fluorophenyl | 511.6 |
| 9 | 4-trifluoromethylphenyl | 561.7 |
| 10 | 4-t-butyl-phenyl | 549.8 |
| 11 | 4-bromophenyl | 572.6 |
| 12 | 4-chlorophenyl | 528.1 |
| 13 | trifluoromethyl | 485.6 |

TABLE 1-continued

Representative Compounds of Formula (I)

| ID No. | $R^3$ | Measured MW |
|---|---|---|
| 14 | 4-cyanophenyl | 518.7 |
| 15 | 4-methoxyphenyl | 523.7 |
| 16 | 2-fluorophenyl | 511.6 |
| 17 | 3-fluorophenyl | 511.6 |
| 18 | 3,5-difluoro-phenyl | 529.6 |
| 19 | 2-chlorophenyl | 528.1 |
| 20 | 3-chlorophenyl | 528.1 |
| 21 | 2-bromophenyl | 572.6 |
| 22 | 2-trifluoromethyl-phenyl | 561.7 |
| 23 | 3-trifluoromethyl-phenyl | 561.7 |
| 24 | 2-methylphenyl | 507.7 |
| 25 | 3-methylphenyl | 507.7 |
| 26 | 2-pyridyl | 494.6 |
| 27 | 3-pyridyl | 494.6 |
| 28 | 4-pyridyl | 494.6 |
| 29 | 3-thienyl | 499.7 |
| 30 | methoxy-methyl- | 461.6 |
| 31 | dimethylamino-methyl- | 474.7 |

Additional representative compounds of formula (I) are as listed in Table 2 below.

TABLE 2

Representative Compounds of Formula (II)

| ID No. | Structure | Measured MW |
|---|---|---|
| 32 | (structure) | 418.54 |
| 33 | (structure) | 419.57 |

TABLE 2-continued

Representative Compounds of Formula (II)

| ID No. | Structure | Measured MW |
|---|---|---|
| 34 | 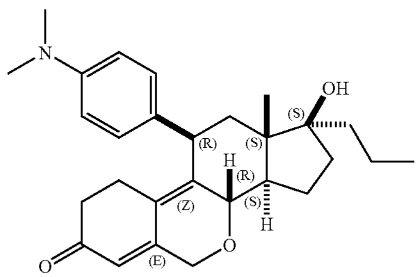 | 435.61 |
| 35 | 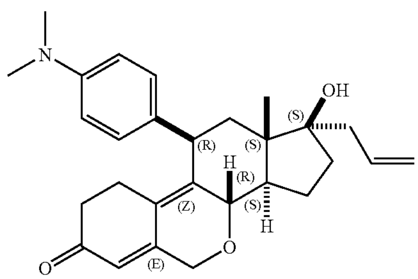 | 433.60 |

Table 3 below, lists additional representative compounds of formula (I) which have been specifically contemplated.

TABLE 3

Prophetic Examples, Compounds of Formula (I)

| ID No. | Structure |
|---|---|
| 36 | 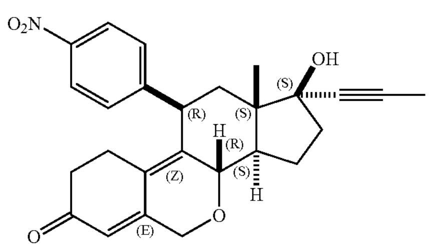 |
| 37 | 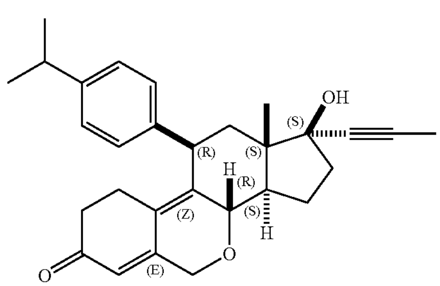 |

TABLE 3-continued

Prophetic Examples, Compounds of Formula (I)

| ID No. | Structure |
|---|---|
| 38 | 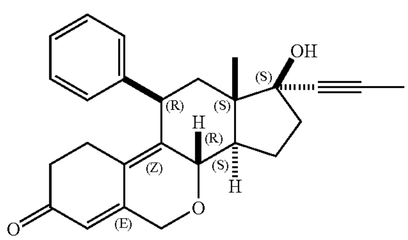 |
| 39 | 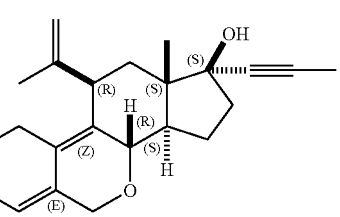 |
| 40 | 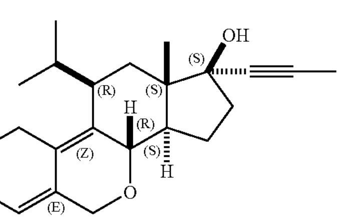 |

TABLE 3-continued

Prophetic Examples, Compounds of Formula (I)

| ID No. | Structure |
|---|---|
| 41 | 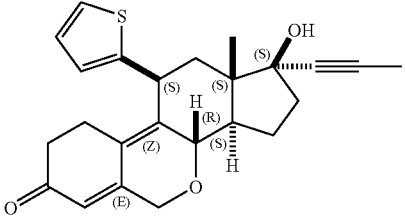 |
| 42 | 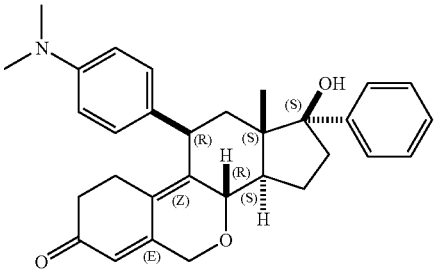 |
| 43 | 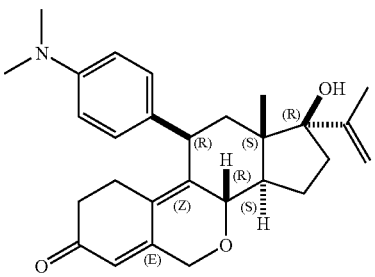 |
| 44 | 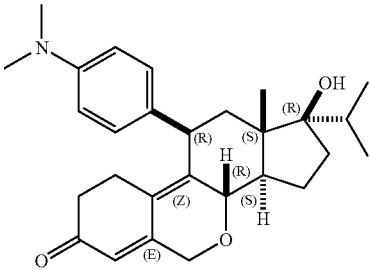 |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$alkyl" shall mean a carbon chain composition of 1-4 carbon atoms.

As used herein, the term "alkenyl" whether used alone or as part of a substituent group, include straight and branched chains comprising at least one unsaturated double bond (preferably one to two, more preferably one unsaturated double bond). For example, alkenyl radicals include —CH=CH$_2$, 2-propenyl, 3-propenyl, 2-butenyl, 3-butenyl, and the like. Unless otherwise noted, "$C_{1-4}$alkenyl" shall mean an alkenyl carbon chain composition of 1-4 carbon atoms.

As used herein, the term "alkynyl" whether used alone or as part of a substituent group, include straight and branched chains. For example, alkenyl radicals include —C≡CH, 2-propynyl, 3-propynyl, 2-butynyl, 3-butynyl, and the like. Unless otherwise noted, "$C_{1-4}$alkynyl" shall mean an alkynyl carbon chain composition of 1-4 carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —CF$_3$, —CH$_2$—CF$_3$, —CF$_2$—CF$_2$—CF$_2$—CF$_3$, and the like.

As used herein, unless otherwise noted, the term "fluorinated $C_{1-4}$alkyl" shall mean any $C_{1-4}$alkyl group as defined above substituted with at least one fluorine atom, preferably substituted with a least one fluoro atom. Suitable examples include but are not limited to —CF$_3$, —CH$_2$—CF$_3$, —CF$_2$—CF$_2$—CF$_2$—CF$_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —OCF$_3$, —OCH$_2$—CF$_3$, —OCF$_2$—CF$_2$—CF$_2$—CF$_3$, and the like.

As used herein, unless otherwise noted, the term "fluorinated $C_{1-4}$alkoxy" shall mean any $C_{1-4}$alkioxy group as defined above substituted with at least one fluorine atom, preferably substituted with a least one fluoro atom. Suitable examples include but are not limited to —OCF$_3$, —OCH$_2$—CF$_3$, —OCF$_2$—CF$_2$—CF$_2$—CF$_3$, and the like.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "$C_{3-8}$cycloalkyl" shall mean any stable 3-8 membered monocyclic, saturated ring system, including cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. Preferably, the heteroaryl is a ring structure containing 5 to 7, more preferably 5 to 6 ring atoms. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include thienyl and pyridyl.

As used herein, the notation "*" shall denote the presence of a stereogenic center.

When a particular group is "substituted" (e.g., phenyl, aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Abbreviations used in the specification, particularly the Schemes and Examples, are as follows:

| | |
|---|---|
| DBU = | 1,8-Diazabicyclo[5.4.0]undec-7-ene |
| DCM = | Dichloromethane |
| DMF = | N,N-Dimethylformamide |
| DMSO = | Dimethylsulfoxide |
| $Et_2O$ = | Diethyl Ether |
| $Et_3N$ = | Triethylamine |
| FBS = | Fetal Bovine Serum |
| HPLC = | High Pressure Liquid Chromatography |
| mCPBA = | 2-(4-Chloro-2-methylphenoxy)-butyric ACid |
| n-BuLi = | n-Butyl Lithium |
| OPTI-MEM = | OPTI-MEM ® Cell Growth Medium |
| OXONE ® = | Potassium monopersulphate salt |
| PR = | Progesterone Receptor |
| TEA = | Triethylamine |
| THF = | Tetrahydrofuran |

As sued herein, unless otherwise noted, the term "disorder mediated by at least one progesterone receptor" shall include any disorder whose symptoms and/or underlying cause may be mediated, treated or prevented by the agonism or antagonism of at least one progesterone receptor. Suitable examples include, butt are not limited secondary amenorrhea; dysfunctional bleeding; uterine leiomyomata; endometriosis; polycystic ovary syndrome; carcinoma of the endometrium, carcinoma of the ovary, carcinoma of the breast, carcinoma of the colon, carcinoma of the prostate, adenocarcinomas of the ovary, adenocarcinomas of the breast, adenocarcinomas of the colon, adenocarcinomas of the prostate, side effects of cyclic menstrual bleeding, and the like. Compounds of the present invention which modulate at least one progesterone receptor are further useful as contraceptives.

As used herein, unless otherwise noted, the term "disorder mediated by at least one glucocorticoid receptor" shall include any disorder whose symptoms and/or underlying cause may be mediated, treated or prevented by the agonism or antagonism of at least one progesterone receptor. Suitable examples include, butt are not limited Type II diabetes mellitus, impaired oral glucose tolerance, elevated glucose levels, Syndrome X, and the like.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Compounds of formula (I) wherein $R^2$ is —OH may be prepared according to the process outlined in Scheme 1.

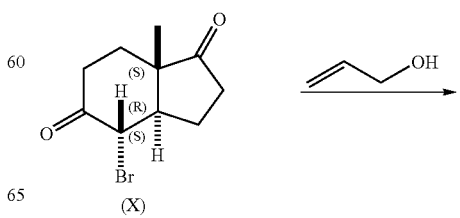

Scheme 1

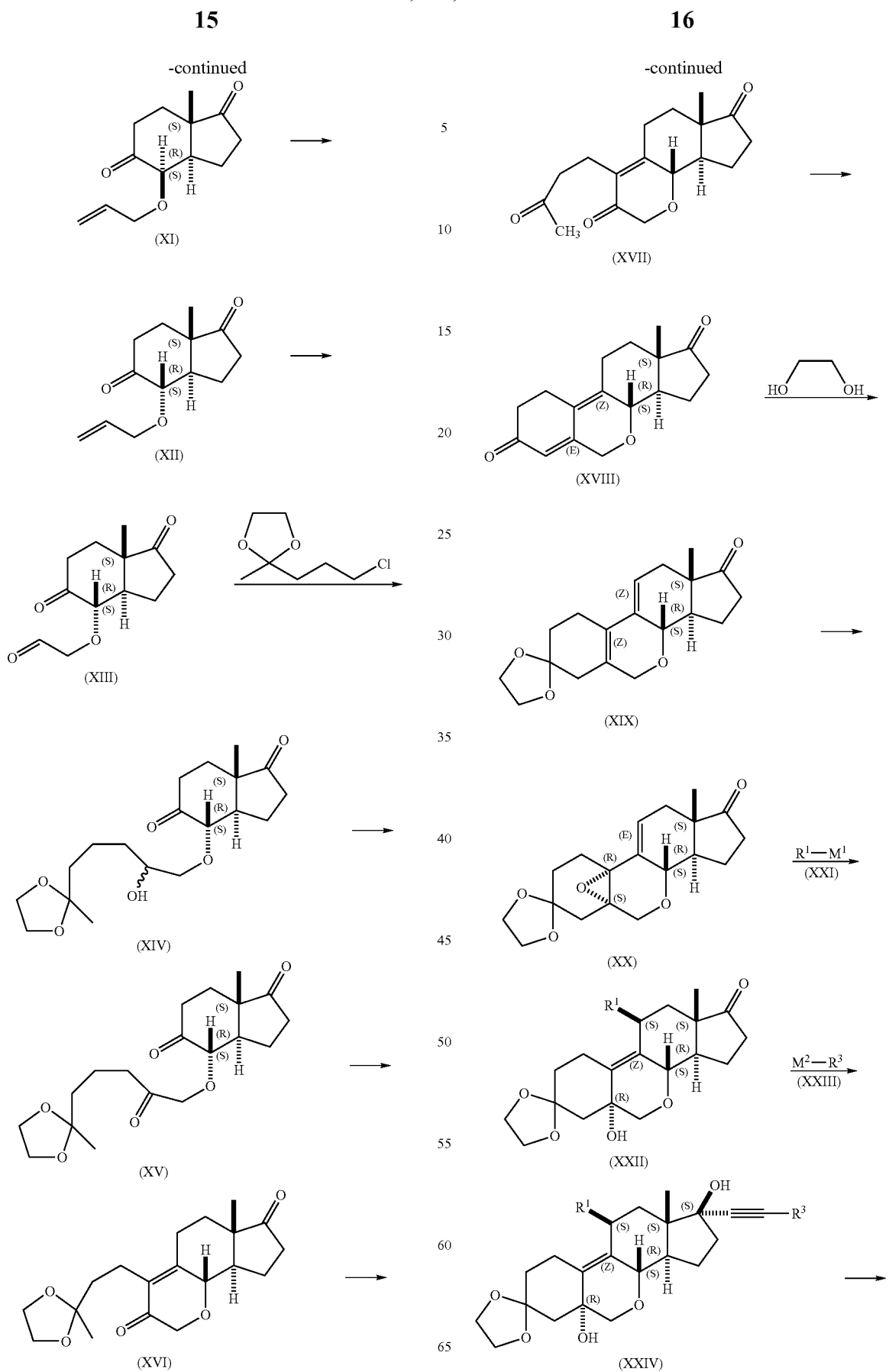

-continued

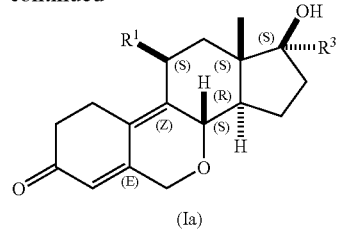

(Ia)

Accordingly, a suitably substituted compound of formula (X), a known compound or compound prepared by known methods, is reacted with prop-2-en-1-ol, a known compound, in the presence of a base such as $Ag_2O$, $Cs_2CO_3$, $K_2CO_3$, $NaOCH_3$, isopropyl-MgCl, n-BuLi, and the like, in an organic solvent such as toluene, THF, DCM, and the like, or in the absence of any solvent, at a temperature in the range of form about −20° C. to about 50° C., preferably at room temperature, to yield the corresponding compound of formula (XI).

The compound of formula (XI) is reacted with a base such as $K_2CO_3$, TEA, $NaOCH_3$, and the like, in an organic solvent such as methanol ethanol, propanol, and the like, at a temperature in the range of form about −20° C. to about 50° C., preferably at room temperature, to yield the corresponding compound of formula (XII).

The compound of formula (XII) is reacted under suitably selected oxidizing conditions, such as $OsO_4$, $KMnO_4$, $CrO_3$, and the like, in the presence of a reagent such as $NaIO_4$, $H_2SO_4$, and the like, in the presence of a base such as 2,6-lutidine, pyridine, $K_2CO_3$, and the like, in a mixture of an organic solvent such as dioxane, tetrahedrofuran, dimethoxymethylene, and the like and water, at a temperature in the range of from about −20° C. to about 50° C., preferably at room temperature, to yield the corresponding compound of formula (XIII).

The compound of formula (XIII) is reacted with 2-(3-chloro-propyl)-2-methyl-[1,3]dioxolane, a known compound or compound prepared by known methods, in the presence of KI and DMF, in the presence of a transition metal catalyst such as cobalt (II) phthalocyanine and a chromium (II) salt such as chromous (II) chloride (which may also be generated in situ by the reduction of a chromium (III) salt such as chromium (III) chloride and a reducing reagent such as a metal, Mn, Zn and the like,) in an organic solvent or mixture of organic solvents such as THF-DMF, THF, dimethoxymethylene, dioxane, DMF, pyridine, and the like, at a temperature in the range of form about −20° C. to about 50° C., preferably at room temperature, to yield the corresponding compound of formula (XIV).

The compound of formula (XIV) is reacted under suitably selected oxidizing conditions, for example by reacting with Dess Martin Periodinane, in an organic solvent such as DCM, dichloroethane, and the like, or reacting under Swern oxidation conditions, in an organic solvent such as DCM, THF, and the like, at a temperature in the range of form about −20° C. to about 50° C., preferably at room temperature, to yield the corresponding compound of formula (XV).

The compound of formula (XV) is reacted with an organic or inorganic base such as $NaOCH_3$, TEA, DBU, and the like, in the presence of an alcohol such as methanol, ethanol, propanol and the like, or in the presence of water, respectively, in an organic solvent such as toluene, benzene, THF, DCM, and the like, at a temperature in the range of form about −20° C. to about 50° C., preferably at about 0° C., to yield the corresponding compound of formula (XVI).

The compound of formula (XVI) is reacted with an acid such as HCl, sulfuric acid, toluenesulfonic acid, trifluroacetic acid, and the like, in an organic solvent such as acetone, THF, dimethoxyethane, dioxane, in the presence of water, and the like, or in water alone, at a temperature in the range of form about −20° C. to about 50° C., preferably at room temperature, to yield the corresponding compound of formula (XVII).

The compound of formula (XVII) is reacted with an inorganic or organic base such as $NaOCH_3$, $Cs_2CO_3$, TEA, DBU, and the like, in the presence of and alcohol such as methanol, ethanol, propanol, and the like or in the presence of water, in an organic solvent such as toluene, THF, DCM, dimethoxyethane, dioxane, and the like, at a temperature in the range of form about −20° C. to about 50° C., preferably at room temperature, to yield the corresponding compound of formula (XVIII).

The compound of formula (XVIII) is reacted with ethane-1,2-diol, a known compound, in the presence of an acid catalyst such as pyridinium hydrochloride, pyridinium toluenesulfonate, ammonium hydrochloride, and the like, in an organic solvent such as benzene, toluene, and the like, with azeotropic removal of water, preferably at reflux, or at a temperature in the range of from about room temperature to about 120° C., to yield the corresponding compound of formula (XIX).

The compound of formula (XIX) is reacted with a suitably selected oxidizing agent such as mCPBA, $H_2O_2$, Oxone®, and the like, in an organic solvent such as DCM, dichloroethane, and the like, at a temperature in the range of form about −70° C. to about room temperature, preferably at about −30° C., to yield the corresponding compound of formula (XX).

The compound of formula (XX) is reacted with a suitably substituted compound of formula (XXI), wherein $M^1$ is MgBr, MgCl, Li or Zn, a known compound or compound prepared by known methods, in the presence of a copper (I) salt such as CuCl, CuBr, CuI, CuCN, or a complex of copper (I) salt and another metal salt such as CuCN-2LiCl, and the like, in an organic solvent such as THF, dimethoxyethane, $Et_2O$, dioxane, and the like, preferably at 0 C, or at −20-50 C to yield the corresponding compound of formula (XXII).

The compound of formula (XXII) is reacted with a suitably substituted compound of formula (XXXIII), wherein $M^2$ is MgBr, MgCl, MgI, Zn or Li, a known compound or compound prepared by known methods, in an organic solvent such as THF, $Et_2O$, dioxane, dimethoxyethane, and the like, at a temperature in the range of form about −20° C. to about 50° C., preferably at room temperature, to yield the corresponding compound of formula (XXIV).

The compound of formula (XXIV) is reacted with an acid such as HCl, sulfuric acid, toluenesulfonic acid, trifluoroacetic acid, and the like, in an organic solvent such as acetone, THF, dioxane, and the like, in the presence of water, or in water alone, at a temperature in the range of form about −20° C. to about 50° C., preferably at room temperature, to yield the corresponding compound of formula (Ia).

One skilled in the art will recognize that compounds of formula (I) wherein $R^2$ is other than —OH may be prepared from the corresponding compound of formula (Ia) according to known methods, for example by O-alkylation, O-acylation, by transformation of a suitably substituted compound of formula (XXIV) to the corresponding compound wherein $R^2$ is $NH_2$, and the like, wherein reactive groups are protected as appropriate and/or necessary.

One skilled in the art will recognize that wherein a reaction step of the present invention may be carried out in a variety of solvents or solvent systems, said reaction step might also be carried out in a mixture of the suitable solvents or solvent systems. Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I) and/or one or more compounds of formula (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.1-5.0 mg/kg/day, preferably from about 0.5-2.5 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating of the present invention may also be carried out using a pharmaceutical composition comprising any of the compounds as defined herein and a pharmaceutically acceptable carrier. The pharmaceutical composition may contain between about 0.1 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

11-(4-Dimethylamino-phenyl)-17-hydroxy-13-methyl-17-prop-1-ynyl-1,2,8,11,12,13,14,15,16,17-decahydro-6H-7-oxa-cyclopenta[a]phenanthren-3-one 15 (Compound #1)

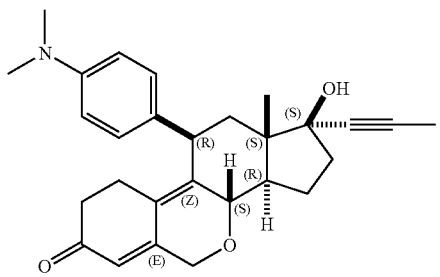

Step A.
4-Allyloxy-7a-methyl-hexahydro-indene-1,5-dione

To the stirred suspension of 4-bromo-7a-methyl-hexahydro-indene-1,5-dione 1 (prepared according to the procedure described in *J. Org. Chem.* 2001, 66, 626.) (2.44 g, 10 mmol), molecular sieves of 4 Å (2.5 g) and silica gel (2.5 g) in allyl alcohol (20 mL) was added Ag$_2$O (2.55 g, 11 mmol) at room temperature. The reaction mixture was stirred at room temperature in the dark for 8 h. The reaction mixture was filtered through a mixture of Celite® and silica gel. The solvent was removed under reduced pressure to yield the title compound as a crude yellow oil.

$^1$H NMR (CDCl$_3$, 400 MHz) (purified sample) 1.31 (s, 3H), 1.64 (m, 1H), 1.7-2.9 (m, 6H), 2.58 (m, 1H), 2.83 (m, 1H), 3.77 (d, 1H), 3.92 (dd, 1H), 4.16 (dd, 1H), 5.18 (d, 1H), 5.28 (d, 1H), 5.86 (m, 1H);

[M+H] 223.1.

Step B.
4-Allyloxy-7a-methyl-hexahydro-indene-1,5-dione

To the stirred solution of the crude 4-allyloxy-7a-methyl-hexahydro-indene-1,5-dione (2.26 g) in methanol (50 mL) at 0° C., was added potassium carbonate (276 mg, 2 mmol). The reaction mixture was allowed to stir at room temperature for 20 h. Saturated ammonium chloride solution (10 mL) was then added to the reaction mixture and the solvent was removed under reduced pressure. The resulting residue was extracted with ethyl acetate (200 mL); the organic layer was dried with brine and sodium sulfate, and then de-colored with charcoal. Flash chromatography using 20% ethyl acetate in hexane yielded the title compound as a colorless oil.

$^1$H NMR (CDCl$_3$, 400 MHz) 1.18 (s, 3H), 1.63 (m, 1H), 1.82 (m, 1H), 2.0 (m, 2H), 2.23 (m, 2H), 2.55 (m, 4H), 3.95 (m, 2H), 4.41 (dd, 1H), 5.20 (d, 1H), 5.29 (d, 1H), 5.91 (m, 1H);

[M+H] 223.1.

Step C. (7a-Methyl-1,5-dioxo-octahydro-inden-4-yloxy)-acetaldehyde

A commercial 4% w/w solution of osmium tetraoxide (10 mL, 0.82 mmol, 0.005 eq) was added to a stirred mixture of 4-allyloxy-7a-methyl-hexahydro-indene-1,5-dione (36.4 g, 164 mmol), 2,6-lutidine (57.2 mL, 246 mmol, 1.5 eq) and sodium periodate (210.6 g, 492 mmol, 3 eq) in dioxane (900 mL) and water (300 mL) at 0° C. The reaction mixture was then allowed to warm slowly to room temperature, and stirred for 24 h. The reaction mixture was cooled to 0° C., and then filtered through a fritted funnel. DCM (1 L) was used to wash to salt cake, and the filtrate was used to extract the separated aqueous solution (4×250 mL). The combined organic layer was dried with magnesium sulfate. The resulting mixture was filtered, condensed and the resulting residue purified by flash chromatography using 20-90% ethyl acetate in hexane yield the title compound as a light yellow foam.

$^1$H NMR (400 MHz, CDCl3) 1.2 (s, 3H), 1.5-2.7 (m, 9H), 4.07 (d, J=7 Hz, 1H), 4.23 (d, J=12 Hz, 1H), 4.44 (d, J=12 Hz, 1H), 9.75 (s, 1H);

[M+H] 225.1.

Step D. 4-[2-Hydroxy-5-(2-methyl-[1,3]dioxolan-2-yl)-pentyloxy]-7a-methyl-hexahydro-indene-1,5-dione Potassium iodide (31.1 g, 187.5 mmol, 3 eq) was added to a solution of 2-(3-chloro-propyl)-2-methyl-[1,3]dioxolane (18.8 mL, 125 mmol, 2 eq) in DMF (50 mL) and the reaction mixture was stirred at 60° C. in dark for 6 h. The reaction mixture was then cooled to room temperature and then combined with (7a-Methyl-1,5-dioxo-octahydro-inden-4-yloxy)-acetaldehyde (14 g, 62.5 mmol) in DMF (150 mL). To the stirred mixture at 0° C., was added cobalt phthalocyanine (357 mg, 0.625 mmol, 0.01 eq), followed by chromous chloride (23.1 g, 187.5 mmol, 3 eq) portion-wise, resulting in release of heat. The reaction mixture was allowed to stir from 0° C. slowly to room temperature for 24 h. The reaction mixture was then cooled to 0° C. and cold water (200 mL) was added. The resulting mixture was extracted with pentane (200 mL). The aqueous layer was extracted with dichloromethane (4×200 mL). The combined organic layer was dried with magnesium sulfate, filtered, the solvent was removed together with toluene (2×100 mL) under reduced pressure, and the resulting residue purified by flash chromatography 20-70% ethyl acetate in hexane to yield the tile compound as an oil, as 1:1 mixture of two diastereomers.

[M+Na] 377.2.

Step E. 7a-Methyl-4-[5-(2-methyl-[1,3]dioxolan-2-yl)-2-oxo-pentyloxy]-hexahydro-indene-1,5-dione Dess-Martin periodinane (10.28 g, 24.24 mmol) was added to a solution of the 4-[2-hydroxy-5-(2-methyl-[1,3]dioxolan-2-yl)-pentyloxy]-7a-methyl-hexahydro-indene-1,5-dione (7.8 g, 22.03 mmol) in dichloromethane (100 mL) at room temperature. The reaction mixture was then stirred at room temperature for 14 h. The reaction was quenched with saturated potassium bicarbonate solution (20 mL). The aqueous solution was extracted with dichloromethane (2×100 mL) and the combined organic layer was dried with magnesium sulfate. The resulting solution was filtered, concentrated and the resulting residue purified by flash chromatography using 30% ethyl acetate in hexane to yield the title compound as an oil.

$^1$H NMR (400 MHz, CDCl3) 1.20 (s, 3H), 1.30 (s, 3H), 1.5-2.8 (m, 15H), 3.92 (m, 4H), 4.04 (d, 1H), 4.16 (d, 1H), 4.48 (d, 1H);

[M+Na] 375.1.

Step F. 3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione A 25% (w/w) solution of sodium methoxide in methanol (2.71 mL, 12.8 mmol, 1 eq) was added to the stirred solution of 7a-Methyl-4-[5-(2-methyl-[1,3]dioxolan-2-yl)-2-oxo-pentyloxy]-hexahydro-indene-1,5-dione (4.5 g, 12.8 mmol, 1 eq) in toluene (200 mL) at 0° C. The reaction mixture was stirred at 0° C. for 1 h, then the reaction was quenched with a 10:1 (v/v) of ammonium chloride/potassium bisulfate solution (100 mL). The aqueous layer was extracted with ethyl acetate (2×100 mL), and the combined organic layer was dried with magnesium sulfate. The resulting solution was then filtered and concentrated to yield the title compound as an oil, which was used in the next step without further purification.

$^1$H NMR (400 MHz, CDCl3) 1.04 (s, 3H), 1.32 (s, 3H), 1.45 (m, 1H), 1.55-2.65 (m, 14H), 2.96 (dd, 1H), 3.94 (m, 4H), 4.04 (d, 1H), 4.25 (m, 2H);

[M+Na] 357.1.

Step G. 3a-Methyl-6-(3-oxo-butyl)-1,2,4,5,9a,9b-hexahydro-3aH-9-oxa-cyclopenta[a]naphthalene-3,7-dione 3 N Hydrochloric acid (0.85 mL) was added to a stirred solution of the crude 3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione in acetone (50 mL) at room temperature. The reaction mixture was stirred at room temperature for 0.5 h. The reaction was quenched with saturated sodium bicarbonate aqueous solution (50 mL), and then the acetone was removed under reduced pressure. The residue was diluted with brine (50 mL), extracted with ethyl acetate (2×100 mL), and the combined organic layer was dried with magnesium sulfate. The resulting solution was filtered and the solvent evaporated to yield an oil, which was used in subsequent steps without further purification.

$^1$H NMR (400 MHz, CDCl3) 1.04 (s, 3H), 1.50 (m, 1H), 1.55-2.65 (m, 17H), 3.05 (dd, 1H), 4.06 (d, 1H), 4.27 (m, 2H);

[M+Na] 313.1.

Step H. 13-Methyl-1,8,11,12,13,14,15,16-octahydro-2H,6H-7-oxa-cyclopenta[a]phenanthrene-3,17-dione A 25% (w/w) solution of sodium methoxide in methanol (2.71 mL, 12.8 mmol, 1 eq) was added to a stirred solution of the crude 3a-Methyl-6-(3-oxo-butyl)-1,2,4,5,9a,9b-hexahydro-3aH-9-oxa-cyclopenta[a]naphthalene-3,7-dione in toluene (200 mL) at 0° C. The resulting mixture was stirred at 0° C. for 0.5 h. The reaction was then quenched with a 10:1 (v/v) of ammonium chloride/potassium bisulfate solution (100 mL). The aqueous layer was extracted with ethyl acetate (2×100 mL), and the combined organic layer was dried with magnesium sulfate. The resulting solution was filtered, evaporated and the residue purified by flash chromatography using 30-50% ethyl acetate in hexane to yield the title compound as a white solid.

$^1$H NMR (400 MHz, CDCl3) 1.02 (s, 3H), 1.42 (m, 1H), 1.7-3.0 (m, 10H), 4.23 (d, 1H), 4.31 (d, 1H), 4.40 (d, 1H), 5.66 (s, 1H);

[M+Na] 273.1.

Step I. 3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione A solution of 13-methyl-1,8,11,12,13,14,15,16-octahydro-2H,6H-7-oxa-cyclopenta[a]phenanthrene-3,17-dione (1.55 g, 5.7 mmol), ethylene glycol (0.32 mL, 5.7 mmol) and pyridinium hydrochloride (0.66 g, 5.7 mmol) in benzene (28.5 mL) was refluxed with a Dean-Stark apparatus for 3 h. The reaction mixture was diluted with ethyl acetate (100 mL), washed with saturated sodium bisulfate solution, and dried with magnesium sulfate. Flash chromatography using 15% ethyl acetate in hexane yielded the title compound as a white solid.

$^1$H NMR (300 MHz, CDCl3) 0.92 (s, 3H), 1.7-2.7 (m, 11H), 4.0 (m, 6H), 4.20 (d, 1H), 5.61 (br s, 1H);

[M+Na] 317.3.

Step J. 3a-Methyl-5,6-epoxy-6-[2-(2-methyl-[1,3]dioxolan-2-yl)-ethyl]-1,2,4,5,9a,9b-hexahydro-3aH-9-oxa-cyclopenta[a]naphthalene-3,7-dione A solution of 70% meta-perobenzoic acid (939 mg, 3.8 mmol) in dichloromethane (20 mL) was added dropwise to a suspension of 3a-methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione (800 mg, 2.53 mmol) and sodium bicarbonate (213 mg, 3.8 mmol) in dichloromethane (51 mL) at –30° C. The resulting mixture was stirred at –30° C. for 16 h. The reaction was then quenched with saturated solution of sodium thiosulfate. The resulting mixture was treated with saturated sodium carbonate solution and then extracted with dichloromethane (2×50 mL). The combined organic layer was dried with magnesium sulfate. The resulting solution was filtered and concentrated to yield the title compound as a white foam.

$^1$H NMR (300 MHz, CDCl3) 0.92 (s, 3H), 1.4-2.7 (m, 13H), 3.63 (d, 1H), 3.72 (d, 1H), 3.95 (m, 5H), 6.11 (br s, 1H);

[M+Na] 333.1.

Step K. 1'-(4-Dimethylamino-phenyl)-6-hydroxy-3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione A 0.5 M solution of 4-N,N-dimethylaminophenyl magnesium bromide (22.9 mL, 11.45 mmol) in THF was added quickly to a solution of copper cyanide (515 mg, 5.72 mmol) and lithium chloride (481 mg, 11.45 mmol) in THF (10 mL) at 0° C., followed by immediate addition of a solution of 3a-methyl-5,6-epoxy-6-[2-(2-methyl-[1,3]dioxolan-2-yl)-ethyl]-1,2,4,5,9a,9b-hexahydro-3aH-9-oxa-cyclopenta[a]naphthalene-3,7-dione (380 mg, 1.15 mmol) in THF (6 mL) at 0° C. The reaction mixture was stirred at 0° C. for 0.5 h, then allowed to stir at room temperature for 0.5 h. The reaction was quenched with saturated ammonium chloride solution and extracted with ethyl acetate (3×50 mL). The organic layer was dried with magnesium sulfate. The resulting solution was filtered, concentrated and the resulting residue was purified by flash chromatography using 50% ethyl acetate in hexane to yield the title compound as a yellow foam.

$^1$H NMR (400 MHz, CDCl3) 0.55 (s, 3H), 1.3-2.5 (m, 13H), 2.92 (s, 6H), 3.60 (d, 1H), 3.99 (m, 5H), 4.21 (d, 1H), 4.32 (d, 1H), 6.66 (d, 1H), 7.08 (d, 1H);

[M+H] 454.2.

Step L. 11-(4-Dimethylamino-phenyl)-17-hydroxy-13-methyl-17-prop-1-ynyl-6-hydroxy-3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione A 0.5 M solution of 1-propynyl magnesium bromide in THF (4.73 mL, 2.37 mmol) was added to a solution of 1'-(4-dimethylamino-phenyl)-6-hydroxy-3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione (134 mg, 0.296 mmol) in THF (3 mL) at room temperature. The resulting mixture was stirred at room temperature for 2 h. The reaction was then quenched with saturated ammonium chloride solution. The resulting mixture was extracted with ethyl acetate (3×50 mL) and the combined organic layer was dried with magnesium sulfate. The resulting solution was filtered, concentrated and the resulting residue purified by flash chromatography to yield the title compound as a crude solid, which was used in subsequent steps without further purification.

$^1$H NMR (400 MHz, CDCl3) 0.55 (s, 3H), 1.3-2.5 (m, 13H), 2.92 (s, 6H), 3.60 (d, 1H), 3.99 (m, 5H), 4.21 (d, 1H), 4.32 (d, 1H), 6.66 (d, 1H), 7.08 (d, 1H);

[M+H] 494.2.

Step M. 11-(4-Dimethylamino-phenyl)-17-hydroxy-13-methyl-17-prop-1-ynyl-1,2,8,11,12,13,14,15,16,17-decahydro-6H-7-oxa-cyclopenta[a]phenanthren-3-one 3N Hydrochloric acid (0.1 mL) was added to a solution of crude 1'-(4-dimethylamino-phenyl)-17-hydroxy-13-methyl-17-prop-1-ynyl-6-hydroxy-3a-Methyl-6-[2-(2-methyl-[1,3]dioxolan-2-yl)-ethyl]-1,2,4,5,9a,9b-hexahydro-3aH-9-oxa-cyclopenta[a]naphthalene-3,7-dione (150 mg) in acetone (10 mL) at room temperature and the reaction mixture stirred at room temperature for 2 h. The reaction was quenched with saturated sodium bicarbonate solution. The acetone was removed under reduced pressure, and the aqueous layer was extracted with ethyl acetate (2×50 mL). The resulting solution was filtered, concentrated and the resulting residue purified by flash chromatography to yield the title compound as a white solid.

$^1$H NMR (400 MHz, CDCl3) 0.58 (s, 3H), 1.55 (m, 1H), 1.88 (s, 3H), 1.9-2.8 (m, 11H), 2.92 (s, 6H), 4.32 (d, 1H), 4.50 (m, 3H), 5.70 (s, 1H), 6.66 (d, 1H), 7.05 (d, 1H);

[M+H] 432.2.

The compounds of Example 2-44, which follow herein, were similarly prepared according to the procedures as described in Scheme 1 and Example 1 above.

Example 2

11-(4-Dimethylamino-phenyl)-17-(4-fluoro-phenyl-ethynyl)-17-hydroxy-13-methyl-1,2,8,11,12,13,14,15,16,17-decahydro-6H-7-oxa-cyclopenta[a]phenanthren-3-one (Compound #8)

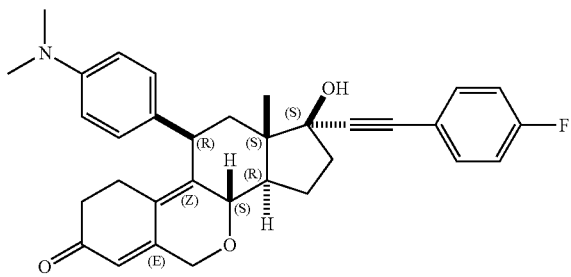

$^1$H NMR (CDCl$_3$, 300 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.03 (m, 4H), 7.42 (m, 2H); [M+H] 511.9.

Example 3

17-(4-Chloro-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #12)

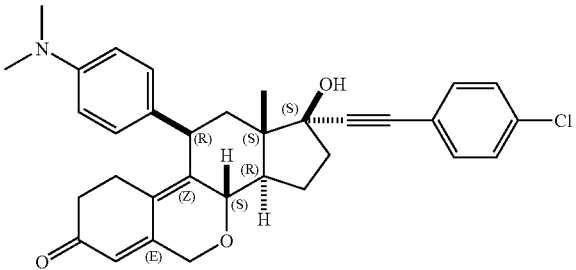

$^1$H NMR (CDCl$_3$, 300 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.03 (d, J=6 Hz, 2H), 7.33 (m, 4H); [M+H] 527.8.

Example 4

11-(4-Dimethylamino-phenyl)-17-hydroxy-13-methyl-7-(4-trifluoromethyl-phenylethynyl)-1,2,8,11,12,13,14,15,16,17-decahydro-6H-7-oxa-cyclopenta[a]phenanthren-3-one (Compound #9)

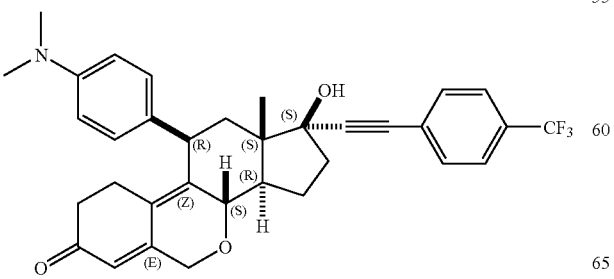

$^1$H NMR (CDCl$_3$, 300 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.03 (d, J=6 Hz, 2H), 7.57 (m, 4H); [M+H] 561.9.

Example 5

17-(3,5-Difluoro-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #18)

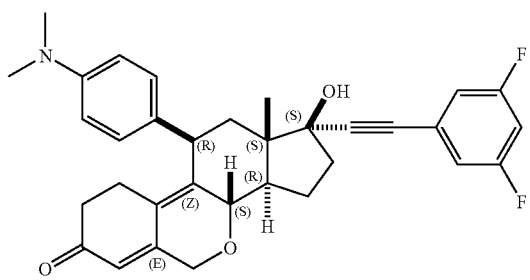

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 6.85 (m, 3H), 7.04 (d, J=6 Hz, 2H); [M+H] 530.2.

Example 6

17-(4-Bromo-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #11)

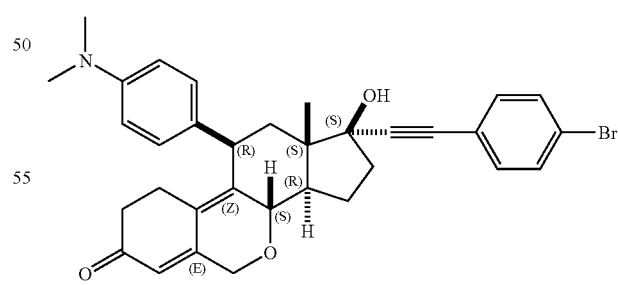

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.30 (d, J=6 Hz, 2H), 7.46 (d, J=6 Hz, 2H); [M+H] 573.7.

Example 7

11-(4-Dimethylamino-phenyl)-17-(3-fluoro-phenyl-ethynyl)-17-hydroxy-13-methyl-1,2,8,11,12,13,14,15,16,17-decahydro-6H-7-oxa-cyclopenta[a]phenanthren-3-one (Compound #17)

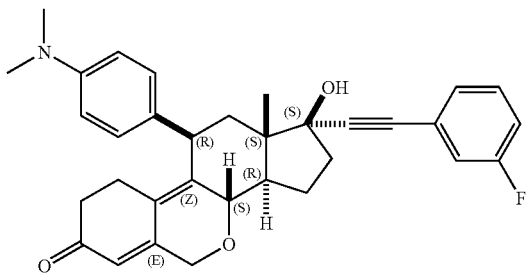

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.2 (m, 4H); [M+H] 512.3.

Example 8

11-(4-Dimethylamino-phenyl)-17-(2-fluoro-phenyl-ethynyl)-17-hydroxy-13-methyl-1,2,8,11,12,13,14,15,16,17-decahydro-6H-7-oxa-cyclopenta[a]phenanthren-3-one (Compound #16)

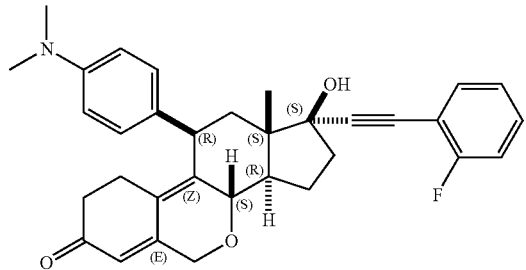

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.25 (m, 4H); [M+H] 512.3.

Example 9

17-(2-Chloro-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #19)

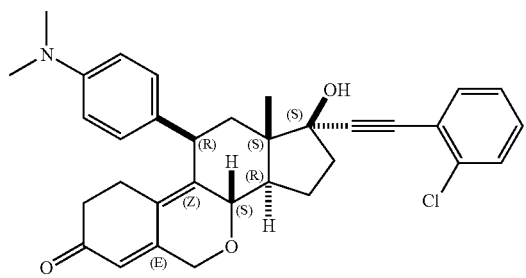

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.35 (m, 4H); [M+H] 528.2.

Example 10

11-(4-Dimethylamino-phenyl)-17-hydroxy-13-methyl-17-phenylethynyl-1,2,8,11,12,13,14,15,16,17-decahydro-6H-7-oxa-cyclopenta[a]phenanthren-3-one (Compound #3)

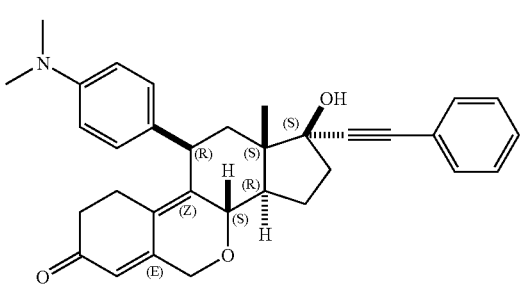

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.38 (m, 4H); [M+H] 494.0.

Example 11

11-(4-Dimethylamino-phenyl)-17-hydroxy-13-methyl-17-(2-trifluoromethyl-phenylethynyl)-1,2,8,11,12,13,14,15,16,17-decahydro-6H-7-oxa-cyclopenta[a]phenanthren-3-one (Compound #22)

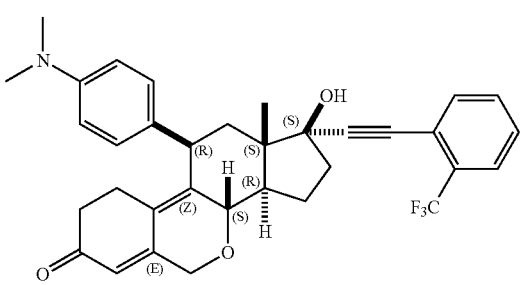

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.55 (m, 4H); [M+H] 562.2.

Example 12

11-(4-Dimethylamino-phenyl)-17-hydroxy-13-methyl-17-thiophen-3-ylethynyl-1,2,8,11,12,13,14,15,16,17-decahydro-6H-7-oxa-cyclopenta[a]phenanthren-3-one (Compound #29)

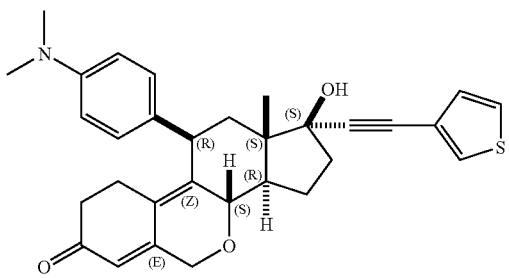

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.66 (d, J=6 Hz, 2H), 7.04 (d, J=6 Hz, 2H), 7.21 (d, J=1 Hz, 1H), 7.27 (d, J=1 Hz, 1H), 7.45 (s, 1H);

[M+H] 500.1.

Example 13

11-(4-Dimethylamino-phenyl)-17-hydroxy-13-methyl-17-p-tolylethynyl-1,2,8,11,12,13,14,15,16,17-decahydro-6H-7-oxa-cyclopenta[a]phenanthren-3-one (Compound #7)

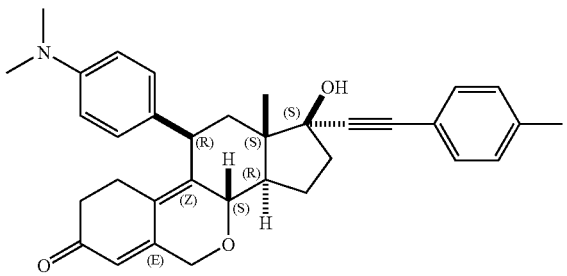

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.12 (d, J=6 Hz, 2H), 7.34 (d, J=6 Hz, 2H);

[M+H] 508.2.

Example 14

11-(4-Dimethylamino-phenyl)-17-hydroxy-13-methyl-17-(3-trifluoromethyl-phenylethynyl)-1,2,8,11,12,13,14,15,16,17-decahydro-6H-7-oxa-cyclopenta[a]phenanthren-3-one (Compound #23)

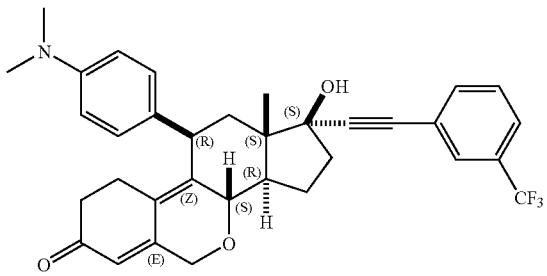

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.55 (m, 4H);

[M+H] 562.2.

Example 15

11-(4-Dimethylamino-phenyl)-17-hydroxy-13-methyl-7-m-tolylethynyl-1,2,8,11,12,13,14,15,16,17-decahydro-6H-7-oxa-cyclopenta[a]phenanthren-3-one (Compound #25)

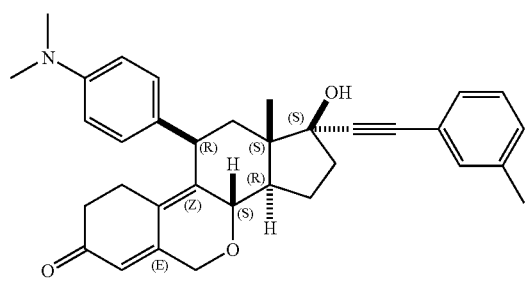

$^1$H NMR (CDCl$_3$, 400 MHz) 0.63 (s, 3H), 1.5-2.8 (m, 11H), 2.31 (s, 3H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.2 (m, 4H);

[M+H] 508.2.

Example 16

11-(4-Dimethylamino-phenyl)-17-hydroxy-17-(4-methoxy-phenylethynyl)-13-methyl-1,2,8,11,12,13,14,15,16,17-decahydro-6H-7-oxa-cyclopenta[a]phenanthren-3-one (Compound #15)

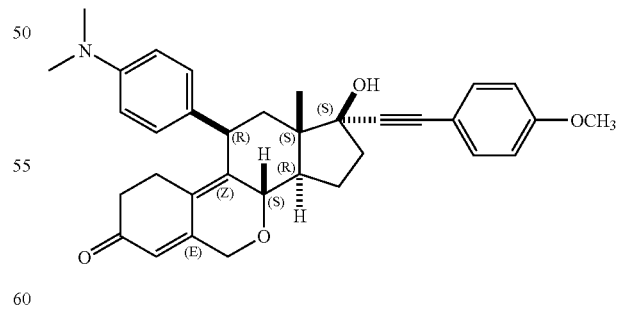

$^1$H NMR (CDCl$_3$, 300 MHz) 0.63 (s, 3H), 1.5-2.8 (m, 11H), 2.92 (s, 6H), 3.71 (s, 3H), 4.37 (d, J=8 Hz, 1H), 4.5 (m, 3H), 5.71 (s, 1H), 6.67 (d, J=6 Hz, 2H), 6.83 (d, J=6 Hz, 2H), 7.04 (d, J=6 Hz, 2H), 7.39 (d, J=6 Hz, 2H);

[M+H] 524.2.

Example 17

4-[11-(4-Dimethylamino-phenyl)-17-hydroxy-13-methyl-3-oxo-1,2,3,6,8,11,12,13,14,15,16,17-dodecahydro-7-oxa-cyclopenta[a]phenanthren-17-ylethynyl]-benzonitrile (Compound #14)

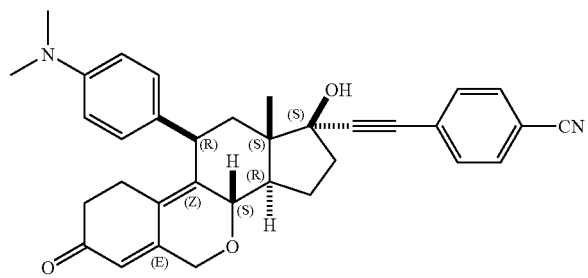

$^1$H NMR (CDCl$_3$, 300 MHz) 0.63 (s, 3H), 1.5-2.8 (m, 11H), 2.92 (s, 6H), 3.71 (s, 3H), 4.37 (d, J=8 Hz, 1H), 4.5 (m, 3H), 5.71 (s, 1H), 6.67 (d, J=6 Hz, 2H), 7.04 (d, J=6 Hz, 2H), 7.58 (m, 4H);
[M+H] 518.8.

Example 18

11-(4-Dimethylamino-phenyl)-17-hydroxy-13-methyl-17-o-tolylethynyl-1,2,8,11,12,13,14,15,16,17-decahydro-6H-7-oxa-cyclopenta[a]phenanthren-3-one (Compound #24)

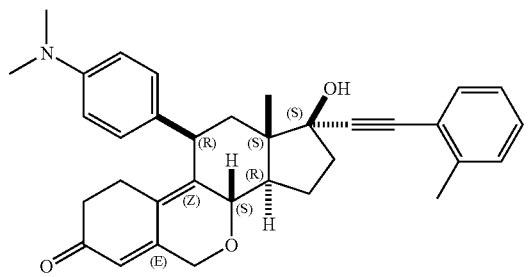

$^1$H NMR (CDCl$_3$, 400 MHz) 0.64 (s, 3H), 1.5-2.8 (m, 11H), 2.42 (s, 3H), 2.92 (s, 6H), 4.37 (d, J=8 Hz, 1H), 4.5 (m, 3H), 5.70 (s, 1H), 6.67 (d, J=6 Hz, 2H), 7.05 (d, J=6 Hz, 2H), 7.25 (m, 4H);
[M+H] 508.2.

Example 19

17-(2-Bromo-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #21)

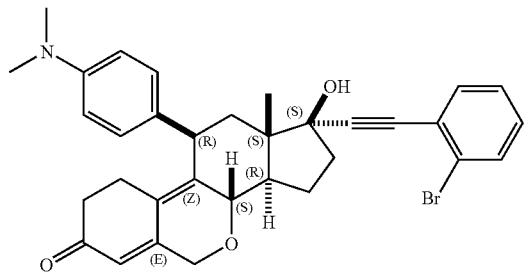

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.35 (m, 4H);
[M+H] 572.1.

Example 20

17-Cyclopropylethynyl-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #2)

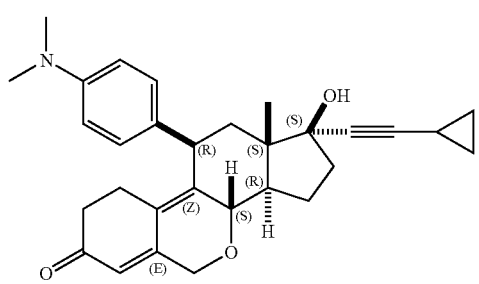

$^1$H NMR (CDCl$_3$, 400 MHz) 0.64 (s, 3H), 0.6-0.8 (m, 4H), 1.5-2.8 (m, 11H), 2.92 (s, 6H), 4.37 (d, J=8 Hz, 1H), 4.5 (m, 3H), 5.70 (s, 1H), 6.67 (d, J=6 Hz, 2H), 7.05 (d, J=6 Hz, 2H);
[M+H] 458.0.

Example 21

17-(3-Chloro-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #20)

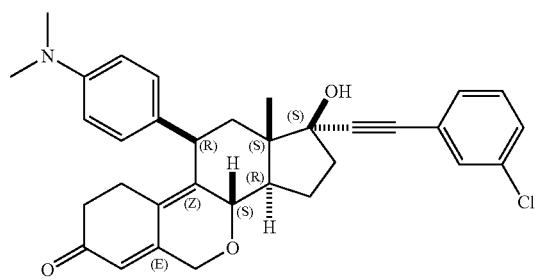

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H), 7.35 (m, 4H);
[M+H] 528.2.

Example 22

11-(4-Dimethylamino-phenyl)-17-hydroxy-13-methyl-17-trifluoroprop-1-ynyl-1,2,8,11,12,13,14,15,16,17-decahydro-6H-7-oxa-cyclopenta[a]phenanthren-3-one (Compound #13)

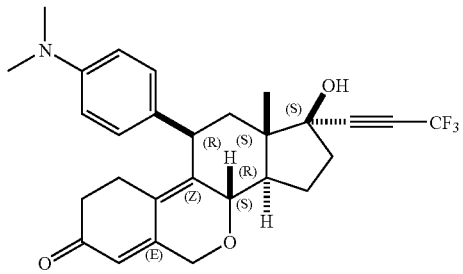

$^1$H NMR (CDCl$_3$, 300 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H);
[M+H] 486.1.

Example 23

11-(4-Dimethylamino-phenyl)-17-ethynyl-17-hydroxy-13-methyl-1,2,8,11,12,13,14,15,16,17-decahydro-6H-7-oxa-cyclopenta[a]phenanthren-3-one (Compound #4)

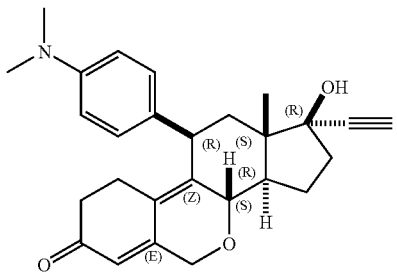

$^1$H NMR (CDCl$_3$, 300 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H);
[M+H] 417.9.

Example 24

11-(4-Dimethylamino-phenyl)-17-(3,3-dimethyl-but-1-ynyl)-17-hydroxy-13-methyl-1,2,8,11,12,13,14,15,16,17-decahydro-6H-7-oxa-cyclopenta[a]phenanthren-3-one (Compound #5)

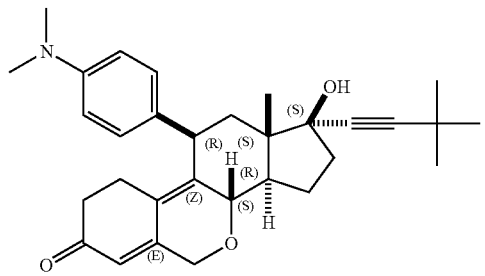

$^1$H NMR (CDCl$_3$, 300 MHz) 0.63 (s, 3H), 1.53 (s, 9H), 1.5-2.8 (m, 11H), 2.92 (s, 6H), 4.37 (d, J=8 Hz, 1H), 4.5 (m, 3H), 5.71 (s, 1H), 6.67 (d, J=6 Hz, 2H), 7.04 (d, J=6 Hz, 2H);
[M+H] 473.9.

Example 25

11-(4-Dimethylamino-phenyl)-17-hydroxy-13-methyl-17-pyridin-2-ylethynyl-1,2,8,11,12,13,14,15,16,17-decahydro-6H-7-oxa-cyclopenta[a]phenanthren-3-one (Compound #26)

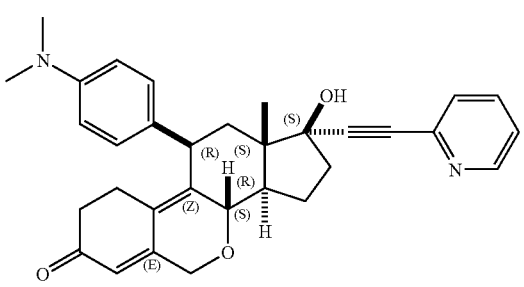

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.71 (s, 1H), 6.66 (d, J=6 Hz, 2H), 7.04 (d, J=6 Hz, 2H), 7.26 (m, 1H); 7.45 (m, 1H), 7.67 (m, 1H), 7.60 (m, 1H);
[M+H] 495.1.

Example 26

11-(4-Dimethylamino-phenyl)-17-hydroxy-13-methyl-17-pyridin-3-ylethynyl-1,2,8,11,12,13,14,15,16,17-decahydro-6H-7-oxa-cyclopenta[a]phenanthren-3-one (Compound #27)

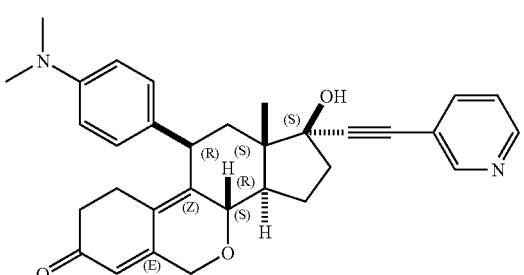

$^1$H NMR (CDCl$_3$, 400 MHz) 0.63 (s, 3H), 1.5-2.8 (m, 11H), 2.92 (s, 6H), 4.37 (d, J=8 Hz, 1H), 4.5 (m, 3H), 5.70 (s, 1H), 6.67 (d, J=6 Hz, 2H), 7.04 (d, J=6 Hz, 2H), 7.27 (m, 1H), 7.72 (m, 1H), 8.53 (m, 1H), 8.69 (m, 1H);
[M+H] 495.1

Example 27

11-(4-Dimethylamino-phenyl)-17-hydroxy-13-methyl-17-pyridin-4-ylethynyl-1,2,8,11,12,13,14,15,16,17-decahydro-6H-7-oxa-cyclopenta[a]phenanthren-3-one (Compound #28)

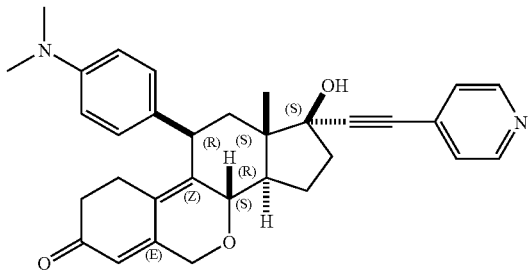

$^1$H NMR (CDCl$_3$, 400 MHz) 0.65 (s, 3H), 1.5-2.8 (m, 11H), 2.92 (s, 6H), 4.5 (m, 3H), 5.71 (s, 1H), 6.68 (d, J=6 Hz, 2H), 7.04 (d, J=6 Hz, 2H), 7.30 (d, J=1 Hz, 2H), 8.59 (d, J=1 Hz, 2H);
[M+H] 495.1.

Example 28

17-(4-tert-Butyl-phenylethynyl)-11-(4-dimethylamino-phenyl)-17-hydroxy-13-methyl-1,2,8,11,12,13,14,15,16,17-decahydro-6H-7-oxa-cyclopenta[a]phenanthren-3-one (Compound #10)

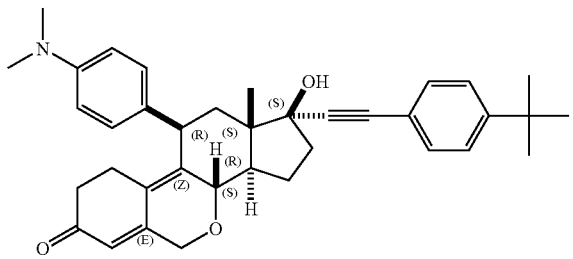

$^1$H NMR (CDCl$_3$, 400 MHz) 0.63 (s, 3H), 1.30 (s, 9H), 1.5-2.8 (m, 11H), 2.92 (s, 6H), 4.37 (d, J=Hz, 1H), 4.5 (m, 3H), 5.71 (s, 1H), 6.66 (d, J=Hz, 2H), 7.04 (d, J=Hz, 2H), 7.38 (m, 4H);
[M+H] 549.9.

Example 29

11-(4-Dimethylamino-phenyl)-17-hydroxy-17-(3-methoxy-prop-1-ynyl)-13-methyl-1,2,8,11,12,13,14,15,16,17-decahydro-6H-7-oxa-cyclopenta[a]phenanthren-3-one (Compound #30)

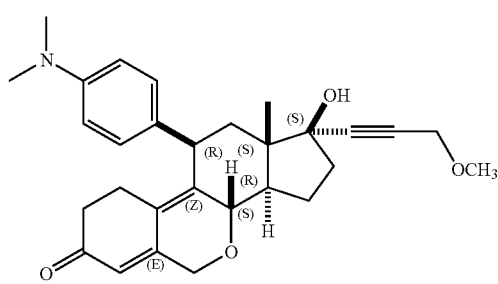

$^1$H NMR (CDCl$_3$, 400 MHz) 0.60 (s, 3H), 1.5-2.8 (m, 11H), 2.92 (s, 6H), 3.40 (s, 3H), 4.16 (s, 2H), 4.34 (d, J=8 Hz, 1H), 4.5 (m, 3H), 5.71 (s, 1H), 6.67 (d, J=6 Hz, 2H), 7.02 (d, J=6 Hz, 2H);
[M+H] 462.1.

Example 30

11-(4-Dimethylamino-phenyl)-17-hydroxy-17-(3-hydroxy-3-methyl-but-1-ynyl)-13-methyl-1,2,8,11,12,13,14,15,16,17-decahydro-6H-7-oxa-cyclopenta[a]phenanthren-3-one (Compound #6)

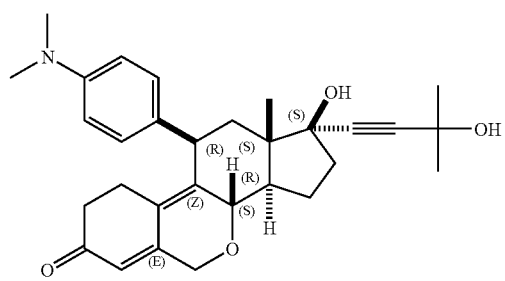

$^1$H NMR (CDCl$_3$, 400 MHz) 0.63 (s, 3H), 1.55 (s, 6H), 1.5-2.8 (m, 11H), 2.92 (s, 6H), 4.37 (d, J=Hz, 1H), 4.5 (m, 3H), 5.71 (s, 1H), 6.66 (d, J=Hz, 2H), 7.04 (d, J=Hz, 2H);
[M+H] 476.2.

Example 31

11-(4-Dimethylamino-phenyl)-17-hydroxy-17-(dimethylamino-methyl)-13-methyl-1,2,8,11,12,13,14,15,16,17-decahydro-6H-7-oxa-cyclopenta[a]phenanthren-3-one (Compound #31)

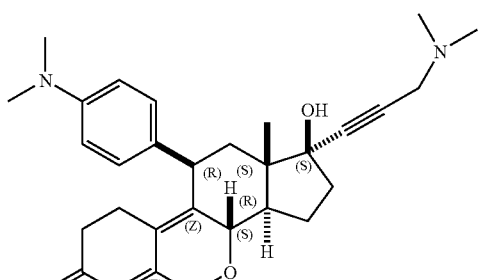

$^1$H NMR (CDCl3, 400 MHz) 0.63 (s, 3H), 1.5-2.8 (m, 11H), 2.92 (s, 6H), 4.37 (d, J=Hz, 1H), 4.5 (m, 3H), 5.71 (s, 1H), 6.66 (d, J=Hz, 2H), 7.04 (d, J=Hz, 2H), 7.58 (m, 4H);
[M+H] 561.9.

Example 32

11-(4-Dimethylamino-phenyl)-17-hydroxy-17-(vinyl)-13-methyl-1,2,8,11,12,13,14,15,16,17-decahydro-6H-7-oxa-cyclopenta[a]phenanthren-3-one (Compound #33)

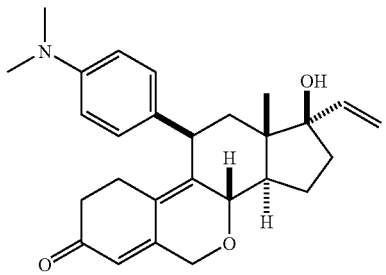

$^1$H NMR (CDCl$_3$, 400 MHz) 0.63 (s, 3H), 1.5-2.8 (m, 11H), 2.92 (s, 6H), 4.37 (d, J=11.2 Hz, 1H), 4.5 (m, 3H), 5.20 (m, 2H), 5.71 (s, 1H), 6.05 (m, 1H), 6.67 (d, J=8.8 Hz, 2H), 7.02 (d, J=8.8 Hz, 2H);

[M+H] 420.3.

Example 33

11-(4-Dimethylamino-phenyl)-17-hydroxy-17-(prop-1-yl)-13-methyl-1,2,8,11,12,13,14,15,16,17-decahydro-6H-7-oxa-cyclopenta[a]phenanthren-3-one (Compound #33)

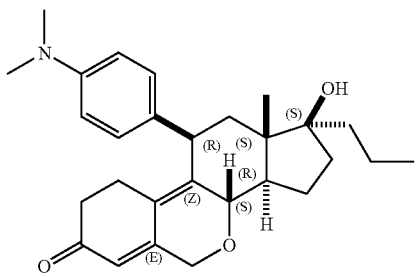

$^1$H NMR (CDCl$_3$, 400 MHz) 0.63 (s, 3H), 1.26 (t, 3H), 1.5-2.8 (m, 15H), 2.92 (s, 6H), 4.37 (d, J=11.2 Hz, 1H), 4.5 (m, 3H), 5.71 (s, 1H), 6.67 (d, J=8.8 Hz, 2H), 7.02 (d, J=8.8 Hz, 2H);

[M+H] 436.3.

Example 34

11-(4-Dimethylamino-phenyl)-17-hydroxy-17-(allyl)-13-methyl-1,2,8,11,12,13,14,15,16,17-decahydro-6H-7-oxa-cyclopenta[a]phenanthren-3-one (Compound #34)

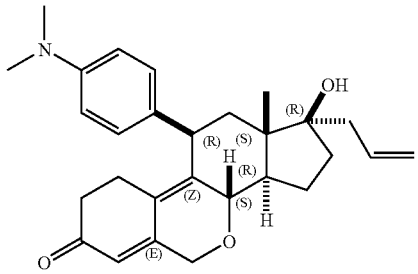

$^1$H NMR (CDCl$_3$, 400 MHz) 0.63 (s, 3H), 1.5-2.8 (m, 11H), 2.92 (s, 6H), 4.37 (d, J=11.2 Hz, 1H), 4.5 (m, 3H), 5.20 (m, 2H), 5.71 (s, 1H), 5.99 (m, 1H), 6.67 (d, J=8.8 Hz, 2H), 7.02 (d, J=8.8 Hz, 2H);

[M+H] 434.2.

Example 35

11-(4-Dimethylamino-phenyl)-17-hydroxy-17-(prop-1-ynyl)-13-methyl-1,2,8,11,12,13,14,15,16,17-decahydro-6H-7-oxa-cyclopenta[a]phenanthren-3-one (Compound #32)

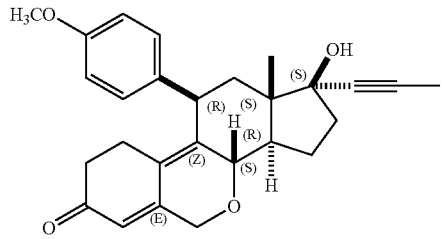

$^1$H NMR (CDCl$_3$, 400 MHz) 0.63 (s, 3H), 1.5-2.8 (m, 11H), 1.88 (s, 3H), 3.80 (s, 3H), 4.37 (d, J=11.2 Hz, 1H), 4.5 (m, 3H), 5.71 (s, 1H), 6.82 (d, J=8.8 Hz, 2H), 7.10 (d, J=8.8 Hz, 2H);

[M+H] 419.1.

Example 36

T47D Human Breast Cancer Cells Assay

T47D human breast cancer cells were grown in RPMI medium without phenol red (Invitrogen) containing 10% (v/v) heat-inactivated fetal bovine serum (FBS; Hyclone), 1% (v/v) penicillin-streptomycin (Invitrogen), 1% (w/v) glutamine (Invitrogen), and 10 mg/mL insulin (Sigma). Incubation conditions were 37° C. in a humidified 5% (v/v) carbon dioxide environment.

The cells were plated in 96-well tissue culture plates at 10,000 cells per well in assay medium [RPMI medium without phenol red (Invitrogen) containing 5% (v/v) charcoal-treated FBS (Hyclone) and 1% (v/v) penicillin-streptomycin (Invitrogen)]. Two days later, the medium was decanted and test compound or control were added at a final concentration of 0.1% (v/v) dimethyl sulfoxide in fresh assay medium. Twenty-four hours later, an alkaline phosphatase assay was performed using a SEAP kit (BD Biosciences Clontech, Palo Alto, Calif.). Briefly, the medium was decanted and the cells were fixed for 30 minutes at room temperature with 5% (v/v) formalin (Sigma). The cells were washed once with room temperature Hank's buffered saline solution (Invitrogen). Equal volumes (0.05 mL) of 1× Dilution Buffer, Assay Buffer and 1:20 substrate/enhancer mixture were then added. After 1 hour incubation at room temperature in the dark, the lysate was transferred to a white 96-well plate (Dynex) and luminescence was read using a LuminoSkan Ascent (Thermo Electron, Woburn, Mass.).

Example 37

A549 Human Lung Cell Assay

A549 Human lung carcinoma cells were grown in F-12K Nutrient Mixture containing 10% (v/v) fetal bovine serum (FBS; Invitrogen), 2 mM glutamine and 0.15% sodium dicarbonate (Invitrogen).

A549 cells were split 1 to 3 in 175 cm tissue culture flask. The cells were incubated at 37° C. in $CO_2$ incubator until the cells were 95% confluent (typically 24-30 hours).

The following solutions were prepared in sterile tubes: (a) Solution A: 1.5 µg/ml of DNA in 8.5 ml OPTI-MEM I Reduced Serum Medium. (GIBCO cat# 31985) and (b) Solution B: 6 µl/ml of DMRIE-C Reagent into 8.5 µl OPTI-MEM I. The two solutions were combined and mixed gently, then incubated at room temperature for 40 minutes.

The A549 cells prepared above were washed with 100 µl of OPTI-MEM I. The medium was removed and 17 ml of the lipid-DNA complex solution was overlayed onto cells. The cells ere then incubated for 16 h at 37° C. in $CO_2$ incubator. The DNA-containing medium was removed and 30 ml of growth medium was added. (5% Charcoal treated FBS) After 5-6 h, the cells were seeded in a 96 well plate and the cells incubated overnight at 37° C. in $CO_2$ incubator.

To each well was then added 5 µl of test compounds and the cells incubated at 37° C. for 10 min. 5 µL of Dexamathasone (CAS [50-02-2]), was then added to each well for challenger and the cells incubated at 37° C. in $CO_2$ incubator for 24 h. 100 µl of Luc-assay buffer was then added into each cell well and the cells incubated for 30 min at room temperature. A 150 µL sample from each well was then transferred into a DYNEX Microlitel plate and read on Top-counter.

Representative compounds of the present invention were tested according to the procedures described in Examples 36-37 above, with results as listed in Table 4, below.

TABLE 4

| ID No. | Biological Results | |
|---|---|---|
| | T47D $IC_{50}$ (nM) | A549 $IC_{50}$ (nM) |
| 1 | 5.15 | 86.49 |
| 2 | 9.55 | 33.38 |
| 3 | 1.38 | 304.01 |
| 4 | 19 | 204.29 |
| 5 | 185 | 166.92 |
| 6 | >1000 | 558.84 |
| 7 | 1.6 | 22.1 |
| 8 | 0.269 | 37.61 |
| 9 | 0.7475 | 111 |
| 10 | 19.5 | 65.79 |
| 11 | 0.9433 | 31.31 |
| 12 | 0.6125 | 43.52 |
| 13 | 18.65 | 55.52 |
| 14 | 3.672 | 41.3 |
| 15 | 3.2 | 80.31 |
| 16 | 1.425 | 65.1 |
| 17 | 1.02 | 56.64 |
| 18 | 0.905 | 34.41 |
| 19 | 1.08 | 64.75 |
| 20 | 12.5 | 48.89 |
| 21 | 8.6 | 62.73 |
| 22 | 3.15 | 51 |
| 23 | 2.65 | 45.39 |
| 24 | 5.8 | 113.23 |
| 25 | 2.85 | 36.26 |
| 26 | 34 | 175.32 |
| 27 | 21 | 341.58 |
| 28 | 39 | 246.5 |
| 29 | 1.55 | 56 |
| 30 | 600 | 315.01 |
| 31 | >1000 | >3000 |

Example 37

As a specific embodiment of an oral composition, 100 mg of the Compound #8 prepared as in Example 2 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

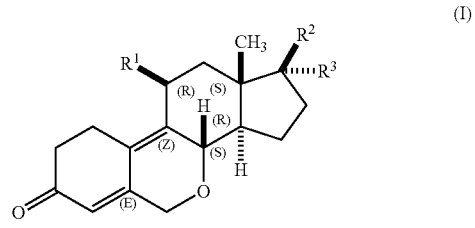

(I)

wherein $R^1$ is selected from the group consisting of $C_{1-6}$alkyl, $C_{2-4}$alkenyl, $C_{2-4}$alkynyl, aryl, heteroaryl, aralkyl and $C_{1-4}$alkyl-heteroaryl; wherein the aryl or heteroaryl, whether alone or as part of a substituent group is optionally substituted with one or more substituents independently selected from hydroxy, carboxy, halogen, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkylamino) and di($C_{1-4}$alkyl)amino;

$R^2$ is selected from the group consisting of $OR^A$, $NR^A R^B$, $SR^A$ and $-SO_2-R^A$; wherein $R^A$ and $R^B$ are each independently selected from the group consisting of hydrogen and $C_{1-4}$alkyl;

$R^3$ is selected from the group consisting of $C_{1-6}$alkyl, $C_{2-4}$alkenyl, $C_{2-4}$alkynyl, aryl, heteroaryl and $-CC-R^4$;

$R^4$ is selected from the group consisting of $C_{1-6}$alkyl, $C_{1-4}$alkyl-OH, $C_{1-4}$alkyl-$NR^C R^D$, halogenated $C_{1-4}$alkyl, $C_{1-4}$alkyl-O—$C_{1-4}$alkyl, $C_{3-8}$cycloalkyl, aryl and heteroaryl selected from the group consisting of pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl and pteridinyl; wherein the aryl or heteroaryl is optionally substituted with one or more substituents independently selected from hydroxy, carboxy, halogen, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkylamino) and di($C_{1-4}$alkyl)amino; and wherein $R^C$ and $R^D$ are each independently selected from the group consisting of hydrogen and $C_{1-4}$alkyl;

or a pharmaceutically acceptable salt thereof.

2. A compound as in claim 1, wherein $R^1$ is selected from the group consisting of $C_{1-6}$alkyl, $C_{2-4}$alkenyl, $C_{2-4}$alkynyl, aryl and heteroaryl; wherein the aryl is optionally substituted with one or more substituents independently selected from halogen, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkylamino) and di($C_{1-4}$alkyl)amino;

$R^2$ is selected from the group consisting of $OR^A$, $SR^A$ and $-SO_2-R^A$; wherein $R^A$ is selected from the group consisting of hydrogen and $C_{1-4}$alkyl;

$R^3$ is selected from the group consisting of $C_{1-6}$alkyl, $C_{2-4}$alkenyl, $C_{2-4}$alkynyl, phenyl, 5- to 6-membered heteroaryl and $-CC-R^4$;

$R^4$ is selected from the group consisting of $C_{1-6}$alkyl, $C_{1-4}$alkyl-OH, $C_{1-4}$alkyl-$NR^CR^D$, fluorinated $C_{1-4}$alkyl, $C_{1-4}$alkyl-O-$C_{1-4}$alkyl, $C_{3-8}$cycloalkyl, aryl and heteroaryl; wherein the aryl is optionally substituted with one to three substituents independently selected from halogen, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkylamino) and di($C_{1-4}$alkyl)amino; and wherein $R^C$ and $R^D$ are each independently selected from the group consisting of hydrogen and $C_{1-4}$alkyl;

or a pharmaceutically acceptable salt thereof.

3. A compound as in claim 2, wherein $R^1$ is selected from the group consisting of phenyl and 5- to 6-membered heteroaryl;

wherein the phenyl is optionally substituted with a substituent selected from the group consisting of $C_{1-3}$alkoxy, amino, ($C_{1-4}$alkylamino) and di($C_{1-4}$alkyl)amino;

$R^2$ is $-OH$;

$R^3$ is selected from the group consisting of $C_{1-4}$alkyl, $C_{2-4}$alkenyl, $C_{2-4}$alkynyl and $-CC-R^4$;

$R^4$ is selected from the group consisting of $C_{1-4}$alkyl, $-C_{1-4}$alkyl-OH, fluorinated $C_{1-3}$alkyl, $-C_{1-3}$alkyl-O-$C_{1-3}$alkyl, $-C_{1-4}$alkyl-$NR^CR^D$, $C_{3-8}$cycloalkyl, phenyl and 5- to 6-membered heteroaryl selected from the group consisting of 2-pyridyl, 3-pyridyl, 4-pyridyl and 3-thienyl; wherein the phenyl is optionally substituted with one to two substituents independently selected from the group consisting of halogen, $C_{1-4}$alkyl, $C_{1-2}$alkyl, fluorinated $C_{1-2}$alkyl and cyano; and wherein $R^C$ and $R^D$ are each independently selected from hydrogen or $C_{1-2}$alkyl;

or a pharmaceutically acceptable salt thereof.

4. A compound as in claim 3, wherein $R^1$ is selected from the group consisting of 4-dimethylamino-phenyl and 4-methoxy-phenyl;

$R^2$ is $-OH$;

$R^3$ is selected from the group consisting of $-CH_2-CH_2-CH_3$, $-CH_2=CH_2$, $-CH_2-CH_2=CH_2$, $-CCH$, $-CC-CH_3$ and $-CC-R^4$;

$R^4$ is selected from the group consisting of t-butyl, $-C(CH_3)_2-OH$, trifluoromethyl, methoxy-methyl-, dimethylamino-methyl-, cyclopropyl, phenyl, 2-methylphenyl, 3-methylphenyl, 4-methylphenyl, 4-t-butylphenyl, 4-methoxyphenyl, 2-trifluoromethylphenyl, 3-trifluoromethylphenyl, 4-trifluoromethylphenyl, 2-fluorophenyl, 3-fluorophenyl, 4-fluorophenyl, 3,5-difluorophenyl, 2-chlorophenyl, 3-chlorophenyl, 4-chlorophenyl, 2-bromophenyl, 4-bromophenyl, 4-cyanophenyl, 2-pyridyl, 3-pyridyl, 4-pyridyl and 3-thienyl;

or a pharmaceutically acceptable salt thereof.

5. A compound as in claim 4, wherein $R^1$ is 4-dimethylamino-phenyl;

$R^2$ is (S)—OH;

$R^3$ is $-CC-R^4$;

$R^4$ is selected from the group consisting of phenyl, 3-methylphenyl, 4-methylphenyl, 4-methoxyphenyl, 2-fluorophenyl, 3-fluorophenyl, 4-fluorophenyl, 3,5-fluorophenyl, 2-chlorophenyl, 4-chlorophenyl, 4-bromophenyl, 2-trifluoromethylphenyl, 3-trifluoromethylphenyl, 4-trifluoromethylphenyl, 4-cyanophenyl and 3-thienyl;

or a pharmaceutically acceptable salt, thereof.

6. A compound as in claim 4, wherein $R^1$ is 4-dimethylamino-phenyl;

$R^2$ is (S)—OH;

$R^3$ is $-CC-R^4$;

$R^4$ is selected from the group consisting of trifluoromethyl, cyclopropyl, 3-methylphenyl, 4-methylphenyl, 3-fluorophenyl, 4-fluorophenyl, 3,5-difluorophenyl, 3-chlorophenyl, 4-chlorophenyl, 4-bromophenyl, 2-trifluoromethylphenyl, 3-trifluoromethylphenyl, 4-cyanophenyl and 3-thienyl;

or a pharmaceutically acceptable salt thereof.

7. A pharmaceutical composition comprising a pharmaceutically acceptable carrier and a compound of claim 1.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method of treating a disorder mediated by a progesterone receptor, wherein the disorder is selected from the group consisting of carcinoma of the breast and adenocarcinomas of the breast, comprising administering to a subject in need thereof a therapeutically effective amount of the compound of claim 1.

11. A method of treating a disorder mediated by a glucocorticoid receptor, wherein the disorder is Type II diabetes mellitus, comprising administering to a subject in need thereof a therapeutically effective amount of the compound of claim 1.

12. A method of treating a disorder mediated by a progesterone receptor, wherein the disorder is selected from the group consisting of carcinoma of the breast and adenocarcinomas of the breast comprising administering to a subject in need thereof a therapeutically effective amount of the composition of claim 7.

13. A method of treating a disorder mediated by a glucocorticoid receptor, wherein the disorder is Type II diabetes mellitus, comprising administering to a subject in need thereof a therapeutically effective amount of the composition of claim 7.

* * * * *